United States Patent [19]

Allen et al.

[11] Patent Number: 5,381,943
[45] Date of Patent: Jan. 17, 1995

[54] ENDOSCOPIC SURGICAL STAPLING INSTRUMENT WITH PIVOTABLE AND ROTATABLE STAPLE CARTRIDGE

[75] Inventors: Eugene D. Allen, Okeana; James J. Bedi, Cincinnati; Gregory D. Bishop, Hamilton; Mark A. Burdorff, Loveland; Sean P. Conlon, Cincinnati; John A. Hibner, Mainville; J. David Hughett, Hamilton; Mark S. Ortiz, Milford; Joseph Paraschac, Cincinnati; Narinderjit Sambi; Thomas J. Sierocuk, both of Mason; Jack E. Smith, Dayton, all of Ohio

[73] Assignee: Ethicon, Inc., Somerville, N.J.

[21] Appl. No.: 959,184

[22] Filed: Oct. 9, 1992

[51] Int. Cl.$^6$ .................................. A61B 17/068
[52] U.S. Cl. ................................ 227/177; 227/19
[58] Field of Search ............. 227/175, 176, 177, 178, 227/179, 180, 19

[56] References Cited

U.S. PATENT DOCUMENTS

| | | | |
|---|---|---|---|
| 2,507,710 | 5/1950 | Grosso | 128/312 |
| 4,427,008 | 1/1984 | Transue | 128/325 |
| 4,562,839 | 1/1986 | Blake et al. | 128/326 |
| 4,566,620 | 1/1986 | Green et al. | 227/19 |
| 4,607,638 | 8/1986 | Crainich | 606/219 |
| 4,664,305 | 5/1987 | Blake et al. | 227/19 |
| 4,691,853 | 9/1987 | Storace | 227/19 |
| 4,728,020 | 3/1988 | Green et al. | 227/19 |
| 4,754,909 | 7/1988 | Barter et al. | 227/19 |
| 4,869,414 | 9/1989 | Green et al. | 227/19 |
| 4,872,456 | 10/1989 | Hasson | 128/321 |
| 4,880,015 | 11/1989 | Nierman | 30/245 X |
| 5,018,657 | 5/1991 | Pedlick et al. | 227/178 |
| 5,040,715 | 8/1991 | Green et al. | 227/8 X |
| 5,042,707 | 8/1991 | Taheri | 606/213 |
| 5,084,057 | 1/1992 | Green et al. | 606/142 |
| 5,125,553 | 6/1992 | Oddsen et al. | 227/175 |
| 5,161,725 | 11/1992 | Murray | 227/176 X |
| 5,174,276 | 12/1992 | Crockard | 128/4 |
| 5,174,487 | 12/1992 | Rothfuss et al. | 227/176 |
| 5,222,975 | 6/1993 | Crainich | 606/219 |
| 5,240,163 | 8/1993 | Stein et al. | 227/175 |
| 5,289,963 | 3/1994 | McGarry et al. | 227/179 |
| 5,312,023 | 5/1994 | Green et al. | 227/175 |
| 5,326,013 | 7/1994 | Green et al. | 227/176 |

FOREIGN PATENT DOCUMENTS 0541987 5/1993 European Pat. Off. .
WO88/01486 3/1988 WIPO .

Primary Examiner—Rinaldi I. Rada

[57] ABSTRACT

A surgical stapler is provided which is insertable through an endoscopic tube to enable a surgeon to staple a hernia patch to tissue inside a body cavity. The endoscopic surgical stapler includes a staple cartridge pivotally mounted on the distal end of a support tube extending from a handle provided with an actuator mechanism for actuating a staple forming mechanism inside the staple cartridge to fasten staples to the tissue. The staple cartridge is adjustable to different angular orientations relative to the support tube. The staple actuator mechanism is operable to actuate the staple cartridge in any of the angular orientations. The support shaft is rotatable about its longitudinal axis relative to the handle to adjust the rotational orientation of the support shaft and the staple cartridge. The staple cartridge is rotatable about its longitudinal axis relative to the support shaft to adjust the rotational position of the staple cartridge relative to the support shaft. Separate actuator mechanisms are provided on the handle to control the pivotal movement of the staple cartridge, the rotation of the support shaft, and the rotation of the staple cartridge relative to the support shaft.

13 Claims, 11 Drawing Sheets

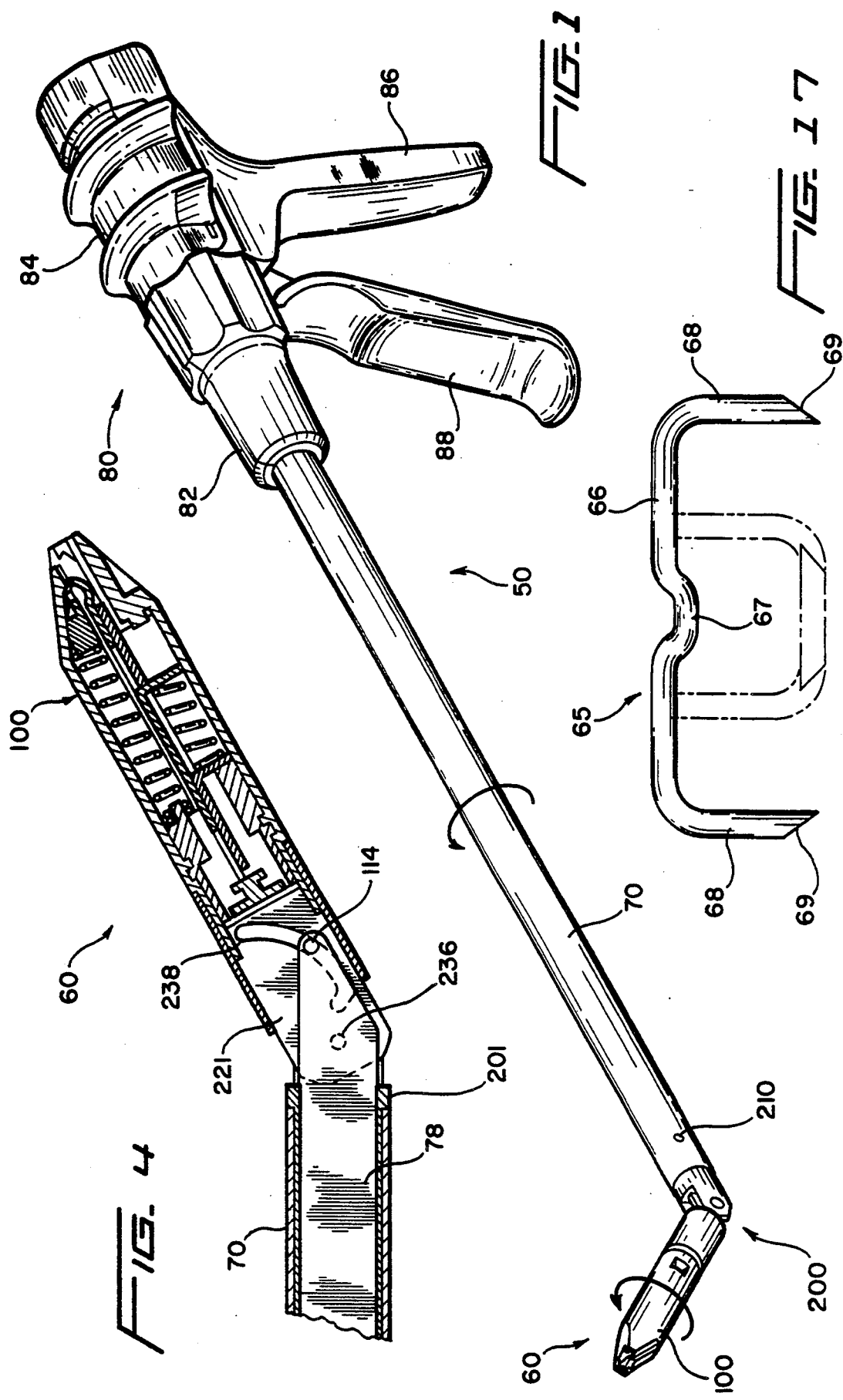

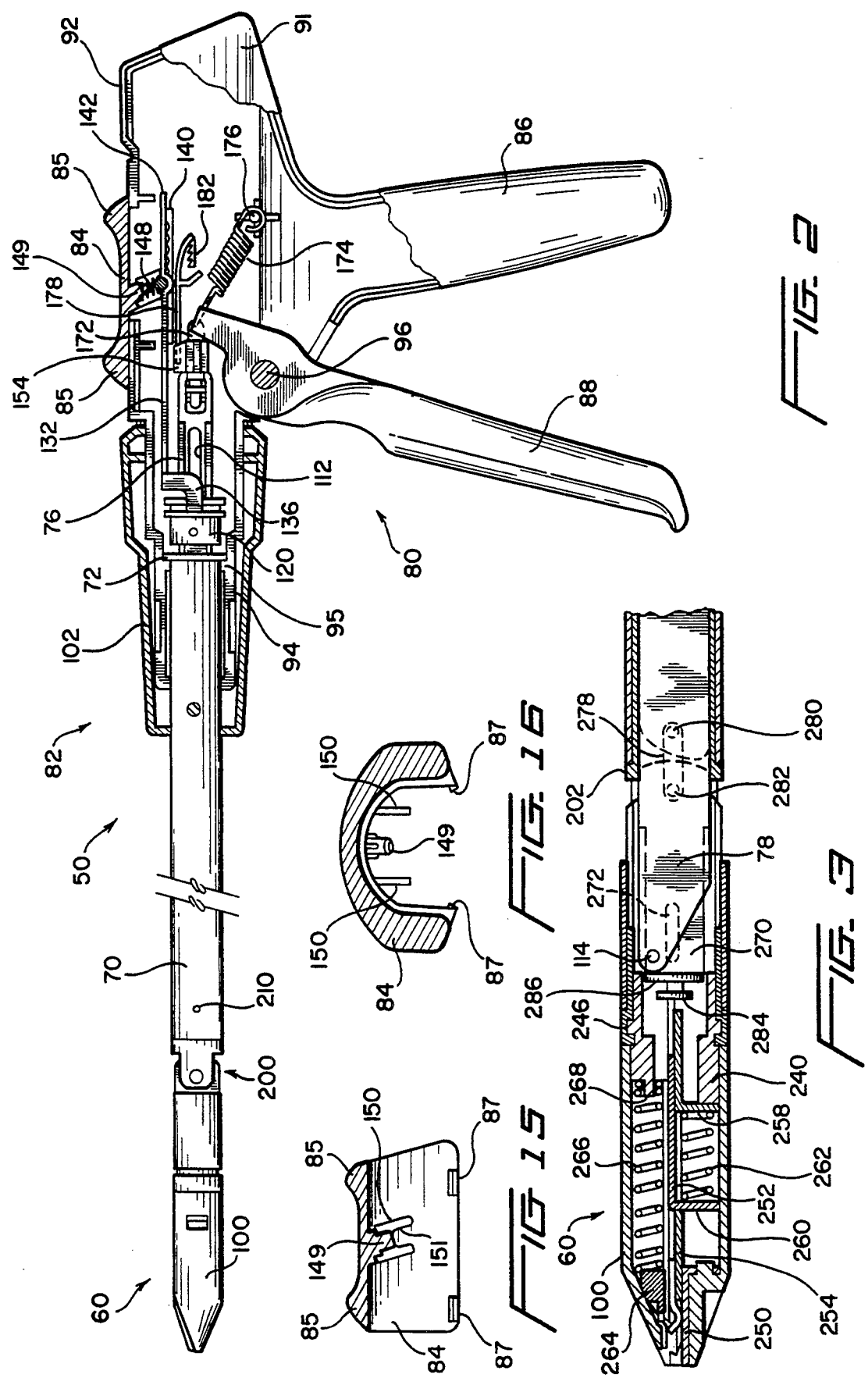

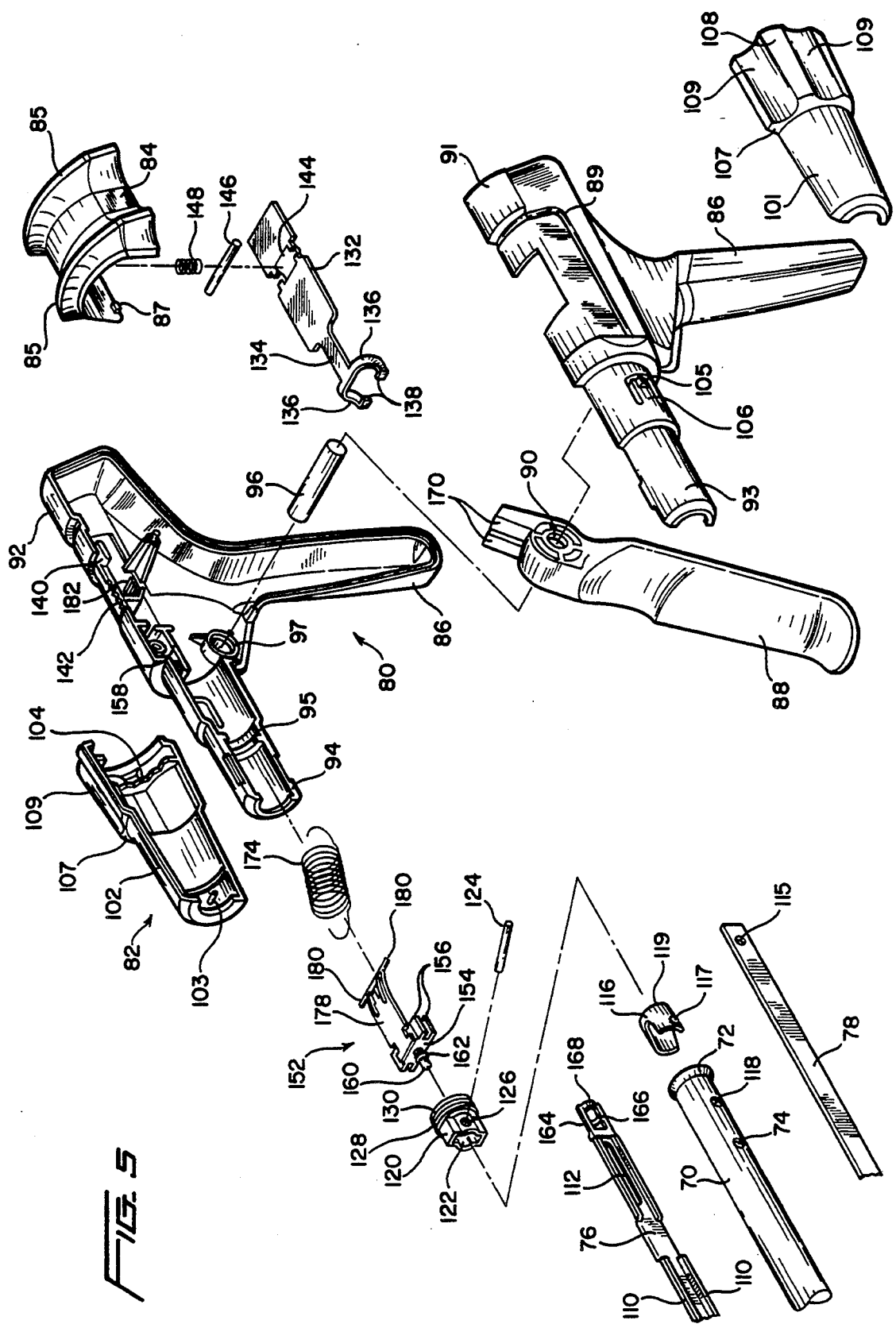

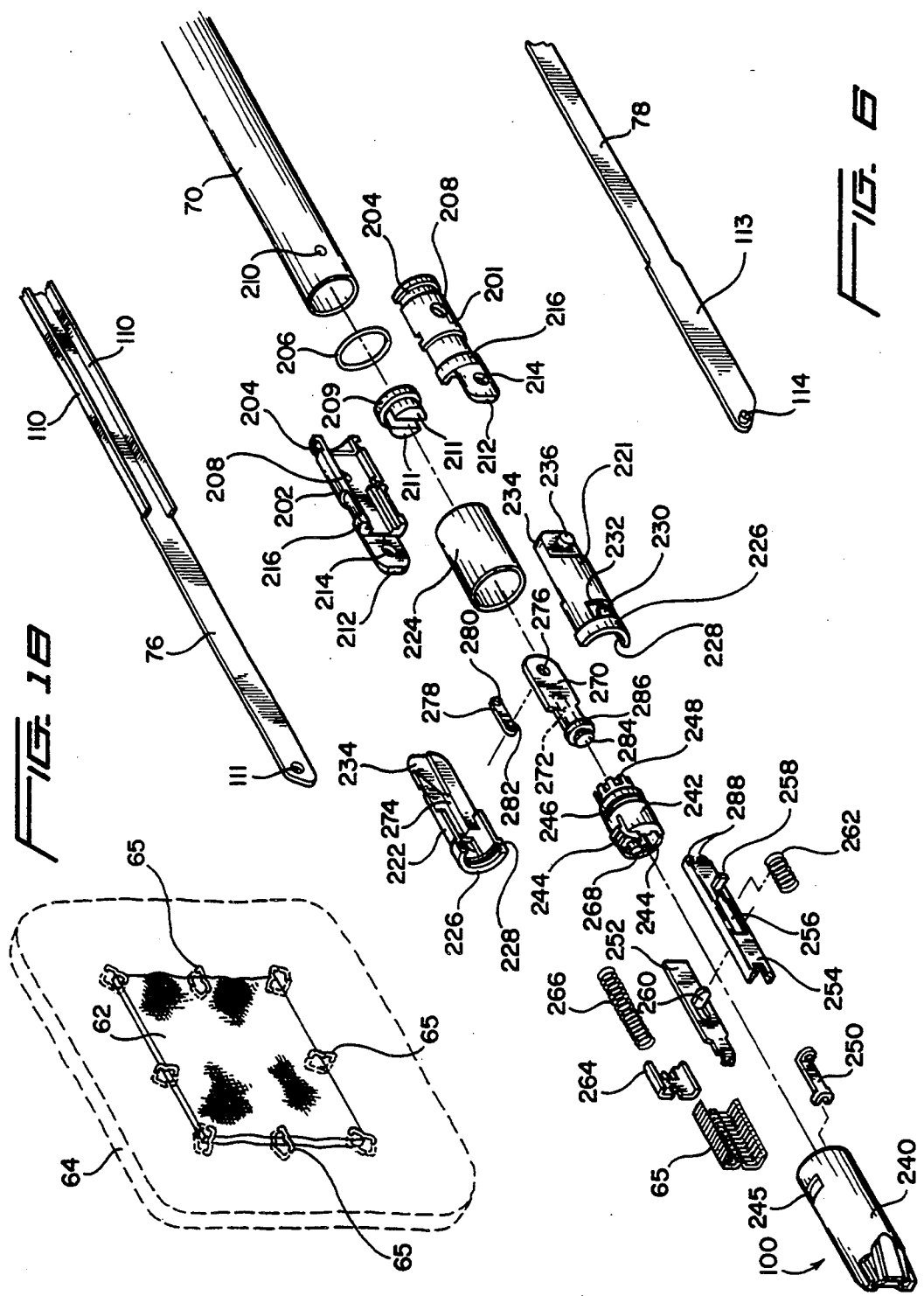

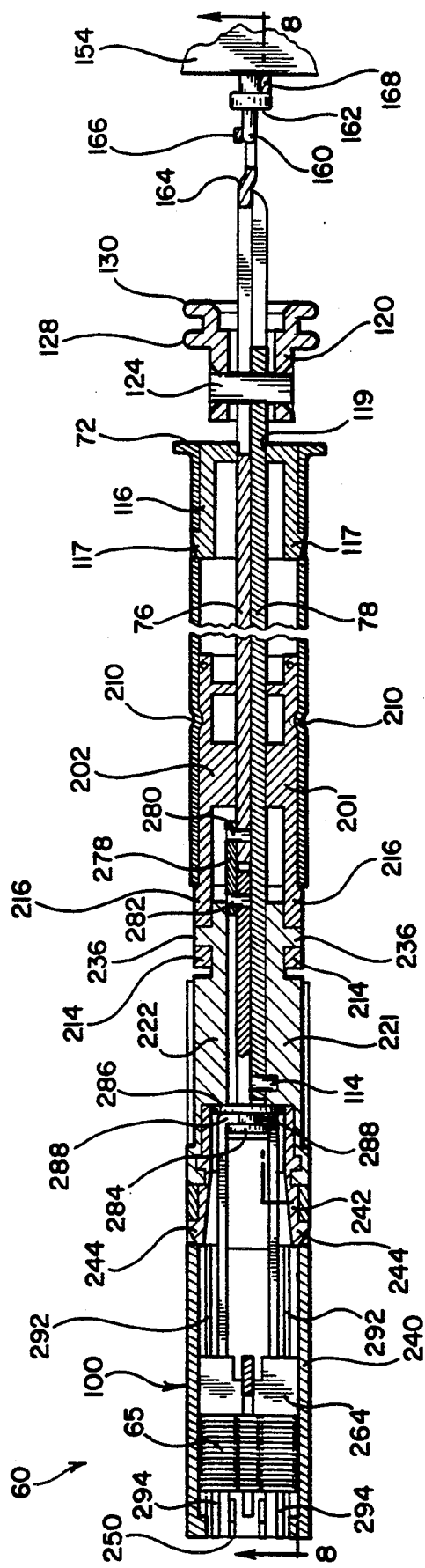
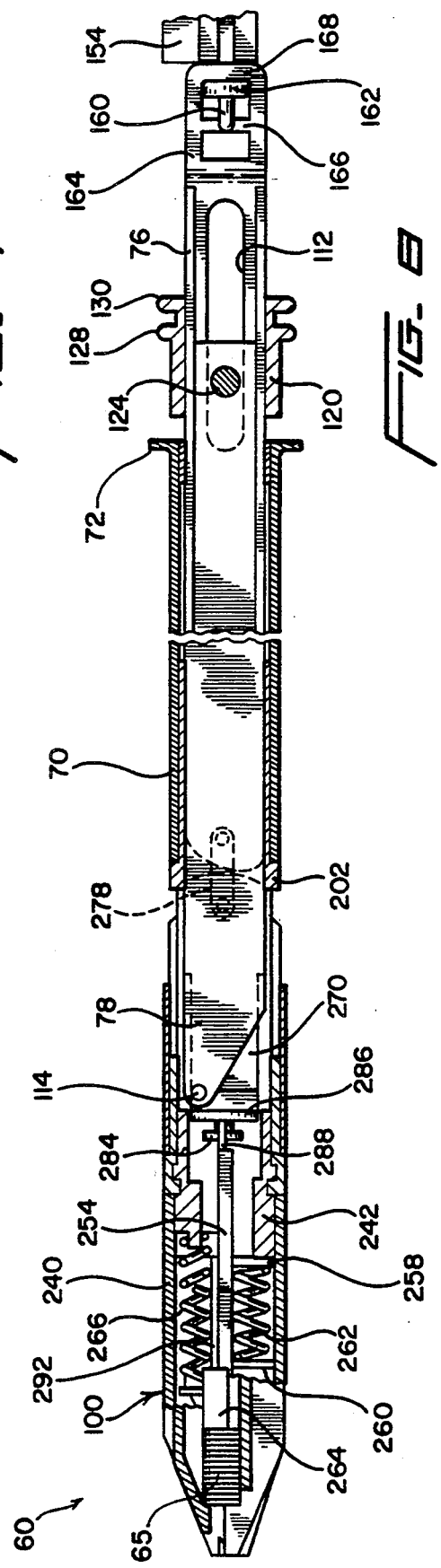

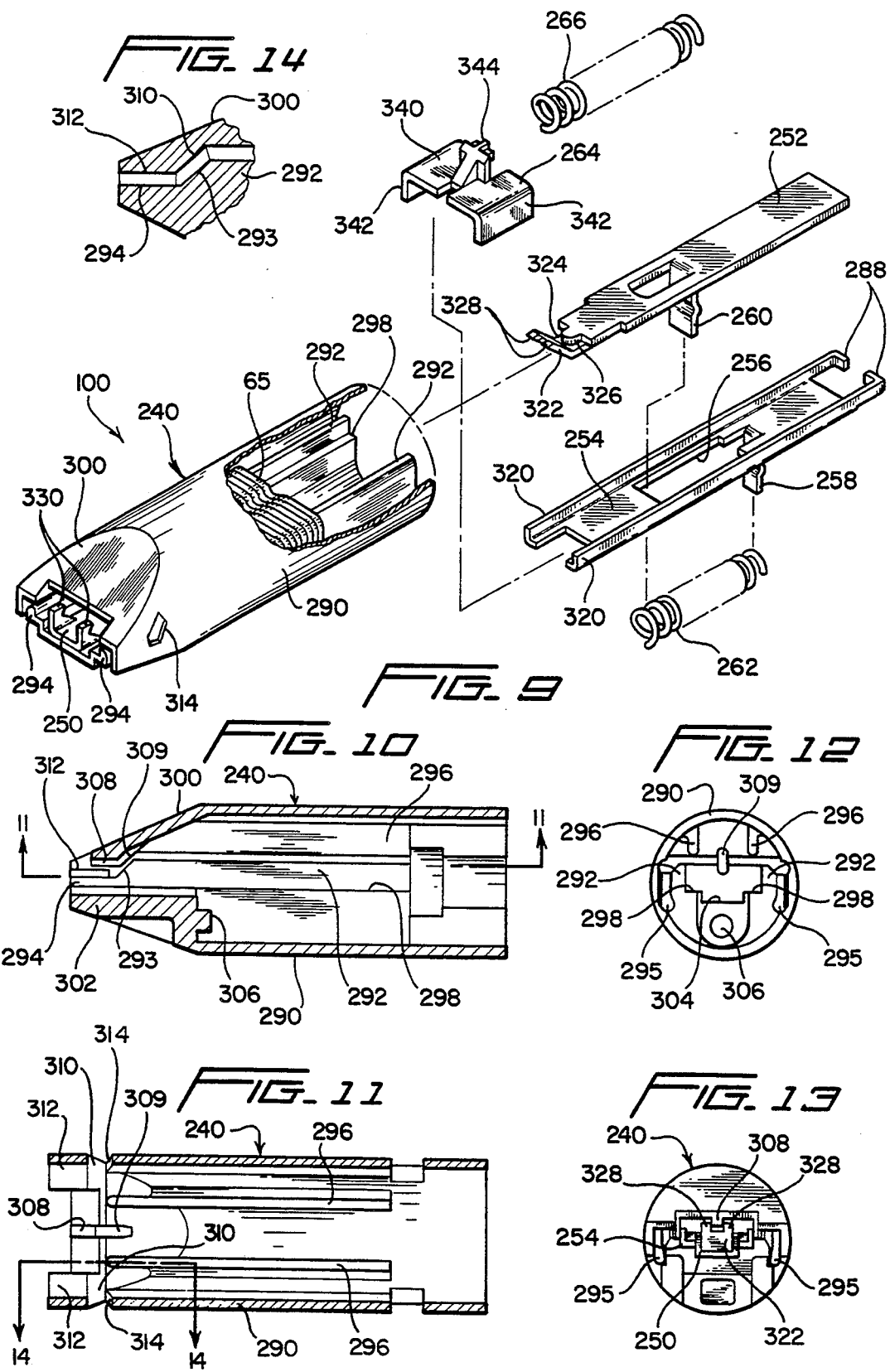

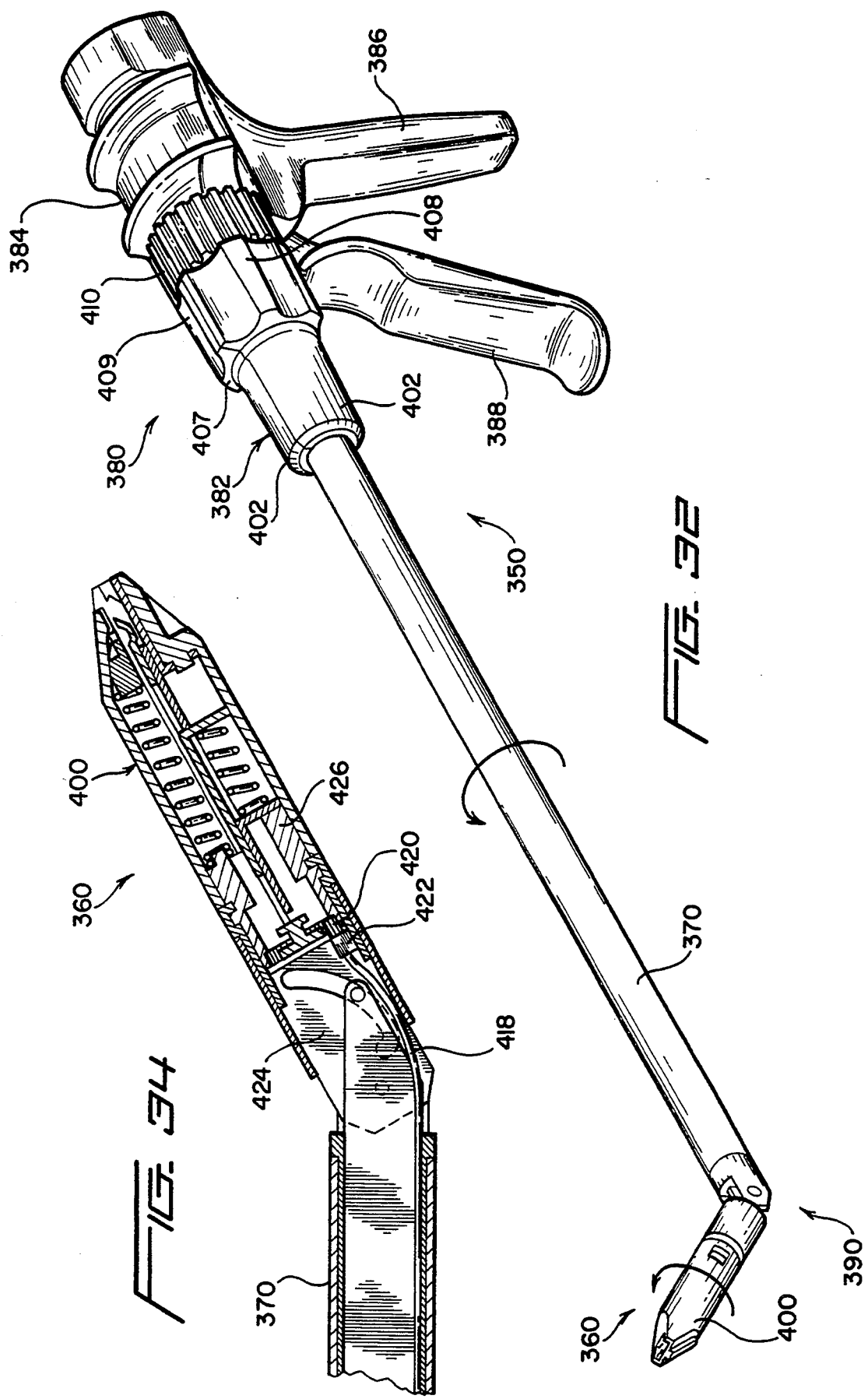

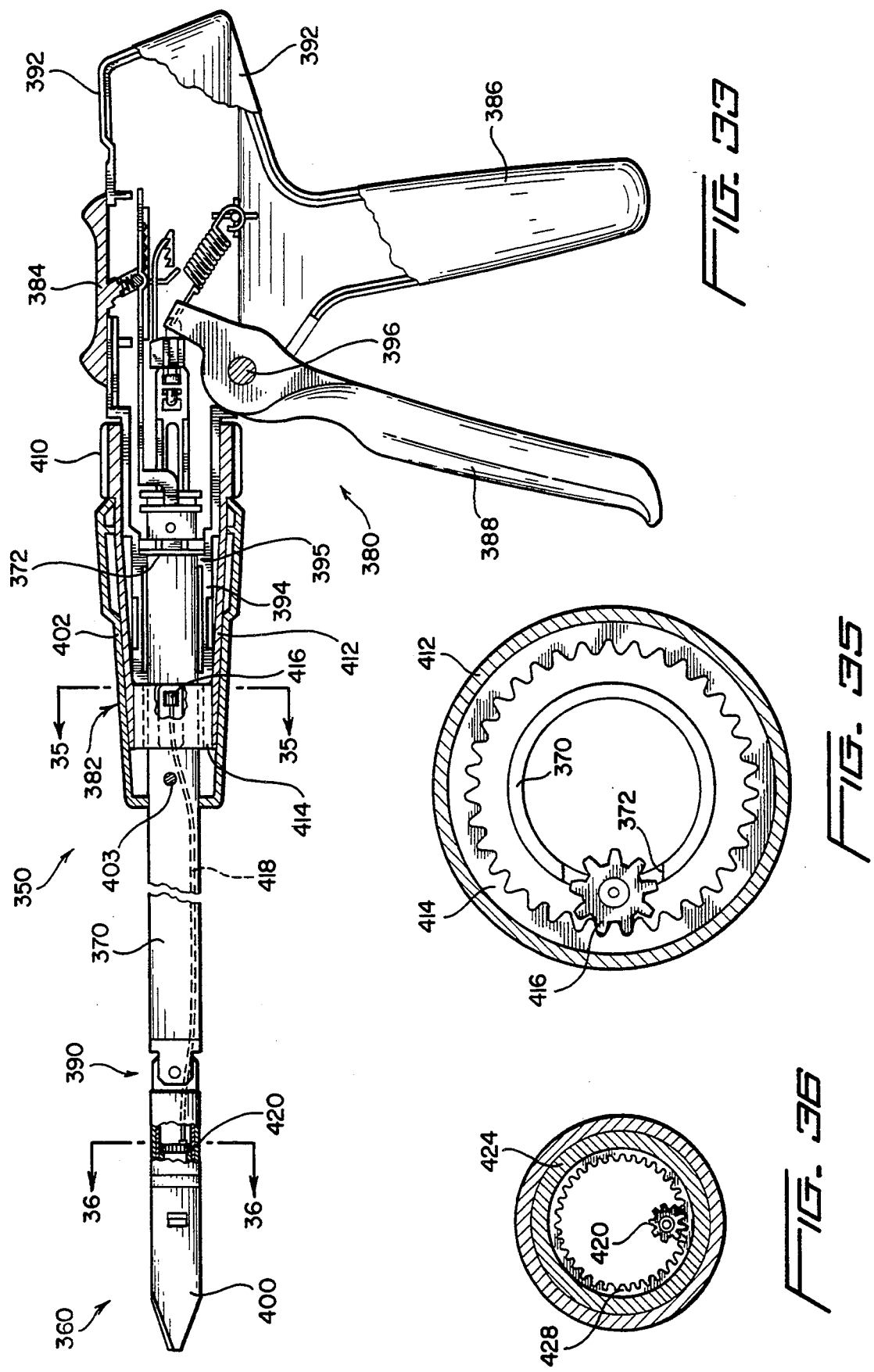

ENDOSCOPIC SURGICAL STAPLING INSTRUMENT WITH PIVOTABLE AND ROTATABLE STAPLE CARTRIDGE

FIELD OF THE INVENTION

The present invention relates to a surgical stapling instrument for applying surgical staples to internal body tissue and, more particularly, to a surgical stapler which can be used endoscopically for the repair of hernias. More specifically, this invention relates to an endoscopic surgical stapling instrument including a staple cartridge which is pivotally and rotatably mounted to allow the surgical staples to be applied to the internal body tissue in any desired orientation. Also, this invention concerns a unique staple cartridge with an improved staple forming mechanism for advancing and fastening the staples to the tissue.

BACKGROUND OF THE INVENTION AND PRIOR ART

With the proliferation of endoscopic surgery, it has been realized that there are many procedures typically performed in open surgery which can be performed endoscopically. A trocar, which is a pointed piercing device, is inserted into the body with a cannula placed around the trocar. After the trocar pierces the abdominal walls, it is removed and the cannula remains in the body. Through this cannula, endoscopic procedures can be conducted. Generally, the endoscopic procedures are performed under insufflation. Some of the more typical procedures have been gall bladder removal, tissue repair and sterilization procedures such as occluding of the fallopian tubes.

Surgeons realize that it may be possible to perform additional procedures endoscopically, once the proper materials and mechanisms become available for performing these procedures. One of the more basic, and quite logical extensions of current endoscopic procedures has been focused on the repair of hernias. It is realized that to have the capability of performing hernia repair endoscopically will benefit the medical community in many ways. Specifically, it is realized that endoscopic hernia repair will allow the patient to recuperate more rapidly, and without the more than likely extensive physical therapy currently practiced as a result of a hernia repair performed by open surgery.

Moreover, it is realized that hernia repair procedures may contain aspects which are applicable in other procedures. For instance, if it is possible to cover, or reinforce and constrain a hernia, it may be possible to apply this procedure to other vessels or organs, in a similar manner. Also, it is realized that once a device becomes available wherein hernias can be repaired, many of the functional components of the hernia repair device will be useful in other devices capable of performing other procedures. Also, naturally, these mechanisms may be useful for procedures in which open surgery is performed.

SUMMARY OF THE INVENTION

Accordingly, it is an object of the present invention to provide an endoscopic surgical stapler for applying staples to secure a hernia repair patch to internal body tissue.

Another object of the invention is to provide an endoscopic surgical stapler including a staple cartridge which is pivotally and rotatably mounted to allow the staples to be fastened to the tissue in any desired orientation.

It is also an object of the invention to provide an endoscopic surgical stapling instrument in which the pivotal movement and rotation of the staple cartridge can be controlled from a remote actuator handle assembly.

It is another object of the invention to provide an endoscopic surgical stapling instrument which facilitates manipulation by a surgeon to control the orientation and acutation of the staple cartridge.

A further object of the invention is to provide a staple cartridge for use with a surgical stapling instrument which includes an improved staple forming mechanism for advancing the staples one at a time into engagement with an anvil about which the staple is formed to secure the staple to the tissue.

The present invention achieves an improved endoscopic surgical stapler which is adapted for insertion through an endoscopic tube or cannula into a body cavity to apply one or more surgical staples to the internal body tissue. The surgical stapling instrument includes a staple cartridge which is pivotally mounted at the distal end of a tubular support shaft extending from a handle which includes a staple actuator mechanism for actuating the staple cartridge to fasten the staples seriatim to the tissue. The staple cartridge is mounted for pivotal movement relative to the support shaft about an axis transverse to the longitudinal axis of the support shaft to permit the angular orientation of the staple cartridge to be adjusted. Also, the staple cartridge is mounted for rotation relative to the support shaft to permit the rotational orientation of the staple cartridge to be adjusted. In addition, the support shaft is rotatable about its longitudinal axis relative to the handle. These features of the stapling instrument allow the staple cartridge to be precisely aligned with the desired region of the internal body tissue to which the staple is applied. Separate actuator mechanisms are provided on the handle for controlling the rotation of the support shaft, the pivoting of the staple cartridge relative to the support shaft, and the rotation of the staple cartridge relative to the support shaft. These actuator mechanisms facilitate manipulation of the stapling instrument by a surgeon to position the staple cartridge in a desired orientation.

In accordance with one aspect of the invention, the surgical stapling instrument is provided with pivot means at the distal end of the support shaft for mounting the staple cartridge for pivotal movement about an axis transverse to the longitudinal axis of the support shaft. Actuator means is provided on the handle for pivoting the staple cartridge about the transverse axis to adjust the angular position of the staple cartridge relative to the support shaft. The stapling instrument includes means for retaining the staple cartridge in different angular positions relative to the support shaft. The staple cartridge has a staple forming mechanism which can be actuated by the staple actuator mechanism with the staple cartridge oriented in any of its different angular positions.

The surgical stapling instrument includes actuator means on the handle for rotating the support shaft about its longitudinal axis to adjust the rotational orientation of the support shaft and the staple cartridge. Also, means is provided for retaining the support shaft in different rotational positions as the support shaft is rotated about its longitudinal axis.

In a preferred embodiment of the surgical stapling instrument, the staple cartridge is mounted for rotation about its longitudinal axis relative to the support shaft. Actuator means is provided on the handle for rotating the staple cartridge to adjust the rotational position of the staple cartridge relative to the support shaft. Also, means is provided for retaining the staple cartridge in different rotational positions as the staple cartridge is rotated about its longitudinal axis relative to the support shaft.

In accordance with another aspect of the invention, a staple cartridge for use with a stapling instrument for applying one or more surgical staples to tissue comprises a cartridge housing adapted to receive a plurality of staples in a row for longitudinal movement therethrough, an anvil mounted on the housing, means for advancing the forwardmost staple in the row into engagement with the anvil, means for rotating the forwardmost staple from a transverse orientation into a longitudinal orientation as the staple is advanced toward the anvil, and means for forming the forwardmost staple about the anvil to attach the staple to the tissue. The staple advancing means comprises a staple holder slidably mounted within the cartridge housing for advancing the forwardmost staple from the row and clamping the staple against the anvil. The staple rotating means comprises ramp means on the cartridge housing for engaging and rotating the forwardmost staple into a longitudinal orientation as the staple is advanced by the staple holder. The staple forming means comprises a staple former slidably mounted within the cartridge housing for movement relative to the staple holder and adapted to form the forwardmost staple about the anvil. Preferably, the staple holder includes an ejector arm for removing the forwardmost staple from the anvil after the staple is formed.

A preferred embodiment of the staple cartridge is adapted for use with a staple having a generally U-shaped body including a crown with a central offset portion and a pair of depending legs at opposite sides of the crown. The staple cartridge comprises an elongated hollow cylindrical cartridge housing including a pair of spaced parallel guide rails therein for slidably supporting a stack of staples for longitudinal movement therealong with the staple crowns resting on the guide rails and the staple legs oriented perpendicularly to the longitudinal axis of the cartridge housing. A staple follower is slidably mounted on the guide rails for urging the staples forwardly on the guide rails toward the distal end of the cartridge housing. An anvil is mounted adjacent to the distal end of the cartridge housing. A staple holder is slidably mounted between the guide rails for engaging the central offset portion of the forwardmost staple to advance the staple from the stack into engagement with the anvil. Ramp means is provided on the cartridge housing for engaging the crown of the forwardmost staple advanced by the staple holder and rotating the staple into a longitudinal orientation with the staple legs oriented parallel to the longitudinal axis of the cartridge housing. A staple former is slidably mounted between the guide rails and movable relative to the staple holder for engaging the crown of the forwardmost staple to form the staple about the anvil to attach the staple to the tissue.

In the preferred embodiment of the staple cartridge, the staple former comprises an elongated channel-shaped member including upstanding side flanges extending along its opposite sides for engaging and forming the staple. The staple holder comprises an elongated plate-like member slidably supported on the staple former and located between the side flanges. The staple holder includes a notch at its distal end for receiving the forwardmost staple to be advanced. The staple holder also includes a pusher finger at its distal end for engaging the forwardmost staple and clamping the staple against the anvil. In addition, the staple holder includes an ejector arm at its distal end for removing the formed staple from the anvil when the staple holder is retracted.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is an overall perspective view of an endoscopic surgical stapling instrument constructed in accordance with this invention;

FIG. 2 is a partially cutaway side view of the stapling instrument of FIG. 1;

FIG. 3 is an enlarged longitudinal section of the stapling head assembly of FIG. 2;

FIG. 4 is an enlarged longitudinal section of the stapling head assembly from the opposite side of FIG. 3;

FIGS. 5 and 6 are exploded perspective views showing the components of the stapling instrument of FIG. 1;

FIG. 7 is an enlarged partially cutaway horizontal section of the stapling head assembly and support shaft of FIG. 2;

FIG. 8 is an enlarged partially cutaway vertical section of the stapling head assembly and support shaft of FIG. 2;

FIG. 9 is an enlarged, exploded perspective view showing the staple cartridge and the staple forming mechanism of the stapling head assembly;

FIG. 10 is an enlarged longitudinal section of the staple cartridge of FIG. 9;

FIG. 11 is an enlarged longitudinal section of the staple cartridge along line 11—11 of FIG. 10;

FIG. 12 is an enlarged proximal end view of the staple cartridge;

FIG. 13 is an enlarged distal end view of the stapling head assembly of FIG. 3;

FIG. 14 is an enlarged fragmentary section of the staple cartridge taken along line 14—14 of FIG. 11;

FIG. 15 is a longitudinal section of a slide actuator for pivoting the stapling head assembly;

FIG. 16 is a proximal end view of the slide actuator of FIG. 15;

FIG. 17 is an enlarged plan view of a staple for use with the surgical stapling instrument of this invention;

FIG. 18 illustrates a hernia repair patch fastened to tissue with staples applied by the surgical stapling instrument of this invention;

FIG. 32 is an overall perspective view of an alternative embodiment of the surgical stapling instrument constructed in accordance with this invention;

FIG. 33 is a partially cutaway side view of the stapling instrument of FIG. 32;

FIG. 34 is an enlarged longitudinal section of the stapling head assembly from the opposite side of FIG. 32;

FIG. 35 is an enlarged cross section of the stapling instrument along line 35—35 of FIG. 33;

FIG. 36 is an enlarged cross section of the stapling instrument along line 36—36 of FIG. 33;

DETAILED DESCRIPTION OF PREFERRED EMBODIMENTS

Figure 19:
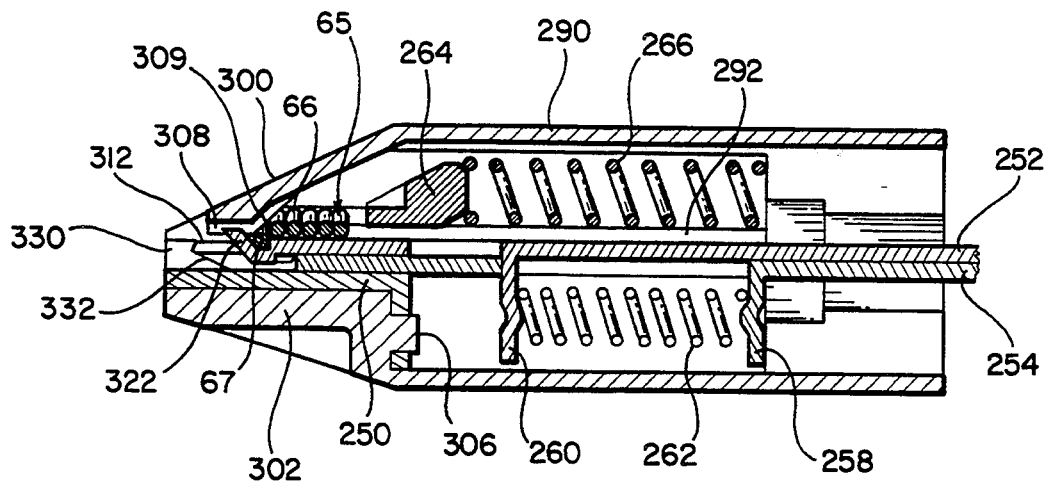
FIG. 19 is an enlarged longitudinal section of the staple cartridge of FIG. 9 showing the staple forming mechanism in a retracted position.

Referring to FIG. 1, the present invention is embodied in an articulating endoscopic surgical stapling instrument, generally 50, including a distal stapling head assembly 60 which is pivotally connected to an elongated support tube 70 rotatably mounted on a proximal actuator handle assembly 80. A rotatable adjusting knob 82 is mounted at the distal end of the actuator handle assembly 80 for rotating the support tube 70 about its longitudinal axis. A saddle-shaped actuator 84 is slidably mounted on the actuator handle assembly 80 for controlling the pivotal movement of the stapling head assembly 60 relative to the support tube 70. The actuator handle assembly 80 includes a depending handle grip 86 and a pivotally mounted staple actuating lever 88 for actuating a staple cartridge 100 on the stapling head assembly 60. Preferably, the actuator handle assembly 80, the adjusting knob 82, the saddle-shaped actuator 84 and the staple actuating lever 88 consist of plastic material.

Referring to FIG. 17, a staple 65 adapted for use with the surgical stapling instrument 50 of the present invention comprises a wire-like body of circular cross section which is bent in a generally U-shaped configuration. Preferably, the staple 65 consists of titanium or stainless steel. The staple 65 includes a top portion or crown 66 provided with a central dimpled portion 67 which is offset downwardly from the crown 66 by an amount approximately equal to the diameter of the circular cross section of the staple 65. The opposite sides of the staple 65 are bent downwardly to provide a pair of depending legs 68 which are substantially perpendicular to the crown 66. Each leg 68 has a beveled end 69 which is beveled at an angle of approximately 45 degrees. When the staple 65 is closed by operation of the surgical stapling instrument 50, the staple legs 68 overlap each other as shown by phantom lines in FIG. 17 to secure the staple to the tissue.

As shown in FIGS. 1 and 5, the handle assembly 80 includes a pair of hollow handle sections 91 and 92 which are adapted to snap fit together. The handle sections 91 and 92 include distally extending elongated, semi-cylindrical neck portions 93 and 94 which receive the proximal end of the support tube 70 therebetween and mount the support tube 70 for rotation about its longitudinal axis relative to the handle assembly 80. Each of the handle sections 91 and 92 includes an internal annular flange 95 (one shown) for engaging a radially projecting flange 72 at the proximal end of the support tube 70 to retain the support tube 70 within the handle assembly 80. The staple actuating lever 88 is pivotally mounted on the actuator handle assembly 80 by a pivot pin 96 extending through a pivot hole 90 in the lever 88. The pivot pin 96 is received in a pair of hollow cylindrical support stems 97 (one shown) formed on the inside of the handle sections 91 and 92.

As shown in FIGS. 1 and 5, the adjusting knob 82 comprises a pair of elongated hollow, tapered sleeve-like sections 101 and 102 which fit together over the neck portions 93 and 94 of the handle sections 91 and 92, respectively. Each of the sleeve-like knob sections 101 and 102 has an inwardly projecting prong 103 adjacent to its distal end. The prongs 103 are received in a pair of holes 74 (one shown) formed on opposite sides of the support tube 70 to secure the knob sections 101 and 102 to the support tube 70. Each of the knob sections 101 and 102 includes a semi-circular ratchet 104 on its inner wall for engaging a pair of detents 105 mounted on resilient arms 106 formed on each of the handle sections 91 and 92. The semi-circular ratchets 104 and the detents 105 provide a ratchet mechanism for retaining the support tube 70 in different rotational positions as the support tube 70 is rotated about its longitudinal axis. For example, each ratchet 104 is provided with eight ratchet teeth which allow the support tube to be rotated in sixteen equal angular increments of 22½ degrees. Each of the knob sections 101 and 102 has an enlarged rear section 107 provided with alternating longitudinal ridges 108 and finger-receiving grooves 109 which facilitate the rotation of the adjusting knob 82 and the support tube 70 by the surgeon.

The support tube 70 is an elongated, thin-walled rigid metal tube, e.g., stainless steel. Inside the support tube 70 are mounted an elongated staple driver 76 and an elongated articulation driver 78 which are slidable longitudinally relative to the support tube 70 and relative to each other. The articulation driver 78 pivots the stapling head assembly 60 in response to movement of the saddle-shaped actuator 84 along the actuator handle assembly 80. The staple driver 76 actuates the staple forming mechanism within the staple cartridge 100 when the staple actuating lever 88 is operated. Preferably, the staple driver 76 and the articulation driver 78 consist of stainless steel.

As shown in FIGS. 5 and 6, the staple driver 76 comprises an elongated thin flat rod including a pair of spaced parallel flanges 110 which extend longitudinally along its top and bottom edges. The staple driver 76 has a pivot hole 111 (FIG. 6) adjacent to its distal end and a longitudinal slot 112 (FIG. 5) adjacent to its proximal end. The articulation driver 78 comprises an elongated thin flat rod which is slidably mounted adjacent to the staple driver 76 and is slidably received between the flanges 110. The articulation driver 78 has an enlarged distal portion 113 (FIG. 6) with a laterally projecting guide pin 114 formed adjacent to its distal end. An assembly hole 115 (FIG. 5) is formed adjacent to the proximal end of the articulation driver 78. A driver guide member 116 of generally cylindrical shape is mounted within the proximal end of the support tube 70. The driver guide member 116 has a pair of opposed, outwardly extending posts 117 which are received in a pair of corresponding holes 118 formed adjacent to the proximal end of the support tube 70. The driver guide 116 has a rectangular slot 119 (FIG. 7) extending therethrough for slidably receiving the staple driver 76 and the articulation driver 78.

As shown in FIGS. 2 and 5, a driver coupling member 120, preferably made of plastic material, includes an opening 122 extending longitudinally therethrough for receiving the proximal ends of the staple driver 76 and the articulation driver 78. The driver coupling member 120 is secured to the articulation driver 78 by a coupling pin 124 which is received in the hole 115 in the articulation driver 78 and extends through a pair of apertures 126 formed on opposite sides of the coupling member 120. The coupling pin 124 is slidably received in the longitudinal slot 112 of the staple driver 76 to allow the articulation driver 78 to slide longitudinally relative to the staple driver 76. A pair of spaced annular flanges 128 and 130 are provided at the proximal end of the coupling member 120 for connection to an articulation control mechanism on the actuator handle assembly 80.

The saddle-shaped actuator 84 (FIG. 5) operates a slide member 132 which is coupled to the driver coupling member 120 to operate the articulation driver 78. The saddle slide member 132 is a generally flat metal plate with an elongated neck 134 projecting distally and having a pair of curved depending arms 136 provided with inwardly projecting fingers 138 which are received between the annular flanges 128 and 130 on the driver coupling member 120. The annular flanges 128 and 130 capture the fingers 138 therebetween and connect the coupling member 120 to the saddle slide member 132 for longitudinal movement therewith. The annular flanges 128 and 130 allow the coupling member 120 to rotate about its longitudinal axis relative to the saddle slide member 132 when the support shaft 70 is rotated by the adjusting knob 82.

The saddle slide member 132 is slidably mounted on a pair of horizontal support ledges 140 (one shown) formed on the interior of the handle sections 91 and 92. Each support ledge 140 includes a series of uniformly spaced notches 142 arranged in a longitudinal row. The saddle slide member 132 is formed with a transverse notch 144 for receiving a ratchet pin 146 which is biased downwardly into the notch 144 by a coil spring 148 mounted on an inclined post 149 formed on the inside of the saddle-shaped actuator 84. A pair of inclined fingers 150 (FIGS. 15 and 16) is formed on the inside of the saddle-shaped actuator 84 and spaced from opposite sides of the post 149. The ratchet pin 146 extends transversely between the fingers 150 and is slidably received in an inclined slot 151 formed in each of the fingers 150.

The opposite ends of the ratchet pin 146 are received in the notches 142 formed in the support ledges 140. The notches 142 and ratchet pin 146 provide a ratchet mechanism for controlling the angular orientation of the stapling head assembly 60 relative to the longitudinal axis of the support tube 70. The notches 142 provide a series of stop positions which correspond to angular orientations preferably of 0, 15, 30, 45 and 60 degrees relative to the longitudinal axis of the support tube 70.

The saddle-shaped actuator 84 includes a pair of outwardly projecting ribs 85 which serve as finger grips to facilitate the longitudinal movement of the saddle-shaped actuator 84 along the handle assembly 60. The saddle-shaped actuator 84 includes a pair of inwardly projecting guides 87 (FIGS. 15 and 16) formed on each of its opposite sides which are snap-fit and slidably received into a pair of longitudinally extending channels 89 (one shown) formed on the exterior of the handle sections 91 and 92.

Referring to FIGS. 2 and 5, the staple actuating mechanism includes a driver link assembly 152 which is coupled to the staple driver 76 and actuated by the staple actuating lever 88. The driver link assembly 152 comprises a block-shaped slide member 154, preferably of plastic material, including a pair of vertically spaced flanges 156 extending from its opposite sides. Each of the handle sections 91 and 92 includes a horizontal support ledge 158 which is received between one pair of the side flanges 156 to slidably support the driver link assembly 152 on the actuator handle assembly 80. A cylindrical connector pin 160 projecting distally from the front of the slide block 154 includes an annular rim 162 for connecting the drive link assembly 152 to the staple driver 76. The connector pin 160 is inserted into a buckle-like connector 164 at the proximal end of the staple driver 76. The buckle-like connector 164 has a pair of longitudinally spaced bands 166 and 168 which are curved outwardly in opposite directions and capture the annular flange 162 therebetween to couple the staple driver 76 and the driver link assembly 152 together for movement along the longitudinal axis of the support tube 70. Also, the buckle-like connector 164 is free to rotate about the axis of the connector pin 160 to allow the staple driver 76 and the articulation driver 78 to rotate when the support tube 70 is rotated about its longitudinal axis.

As shown in FIGS. 2 and 5, the staple actuating lever 88 includes a pair of upright fingers 170 which are spaced apart to receive a rearwardly projecting lug 172 (FIG. 2) formed on the slide member 154. The lug 172 is connected to a return coil spring 174 which is anchored to a post 176 on the handle section 92. The return spring 174 normally urges the slide 154 rearwardly into engagement with the upright arms 170 to retain the staple actuating lever 88 in the unactuated position (FIG. 2).

The driver link assembly 152 includes a rearwardly projecting metal leaf spring 178 which is curved downwardly at its proximal end and provided with a pair of spring arms 180 projecting laterally from its opposite sides for engaging a pair of ratchets 182 (one shown) formed on the handle sections 91 and 92. The spring arms 180 and the ratchets 182 provide a ratchet mechanism which retains the driver link assembly 152 at different stages of advancement as the staple actuating lever 88 is actuated. Once the spring arms 180 are engaged with the ratchets 182, the driver link assembly 152 cannot return to its unactuated position until the stapling head assembly 60 is completely fired by operating the staple actuating lever 88.

Referring to FIGS. 1 and 6, the stapling head assembly 60 is pivotally mounted at the distal end of the support tube 70 for pivotal movement about an axis transverse to the longitudinal axis of the support tube 70. The stapling head assembly 60 is pivotally mounted on the support tube 70 by a pivot connection, generally 200, including a pair of pivot housings 201 and 202 of generally semi-cylindrical shape which are fit together and are inserted into the distal end of the support tube 70. The pivot housings 201 and 202 are generally shaped as hollow semi-cylindrical sleeves for slidably receiving the staple driver 76 and the articulation driver 78. Adjacent to the proximal end of each of the pivot housings 201 and 202 is a semi-circular groove 204 which receives an O-ring 206 for engaging the interior of the support tube 70. The O-ring 206 helps to vent the staple cartridge 100 at the insufflation pressures of the abdominal cavity.

As shown in FIG. 6, each of the pivot housings 201 and 202 includes a side opening 208 formed therein adjacent to the groove 204. When the pivot housings 201 and 202 are assembled, silicone is injected into the side openings 208 about the staple driver 76 and the articulation driver 78. With the pivot housings 201 and 202 inserted into the distal end of the support tube 70, a pair of dimples 210 (FIG. 7) is formed on opposite sides of the support tube 70 to deform the tube material into the side openings 208 to fasten the pivot housings 201 and 202. Alternatively, in place of the injected silicone material, a hollow cylindrical silicone plug 209 (FIG. 6) can be inserted into the proximal ends of the pivot housings 201 and 202. The silicone plug 209 includes a pair of distally projecting flanges 211 which slidably engage the outer surfaces of the staple driver 76 and the articulation driver 78. Each of the pivot housings 201 and 202 includes a distally projecting tang 212 which is provided with a pivot hole 214. The pivot housings 201 and 202 include front semi-circular flanges 216 which engage the distal end of the support tube 70.

The pivot connection 200 includes a pair of clamshell members 221 and 222 which are generally semi-cylindrical in shape and fit together inside a tubular clamshell sleeve 224. The clamshell members 221 and 222 each include a front semi-circular flange 226 which engages the distal edge of the clamshell sleeve 224. The front flanges 226 each include an interior semi-circular groove 228. Each of the pivot housings 221 and 222 includes a detent arm 230 projecting inwardly through a side opening 232. Also, each pivot housing 221 and 222 includes a rearwardly extending tang 234 provided with an outwardly projecting pivot pin 236. The pivot pins 236 on the clamshell members 221 and 222 are pivotally received in the pivot holes 214 on the pivot housings 201 and 202. As shown in FIG. 4, the pivot housing 221 has an arc-shaped groove 238 formed on its interior surface for receiving the guide pin 114 on the articulation driver 78. The arc-shaped groove 238 and the guide pin 114 convert longitudinal movement of the articulation driver 78 into pivotal movement of the stapling head assembly 60. Preferably, the pivot housings 201 and 202 and the clamshell members 221 and 222 consist of plastic material.

Referring to FIG. 6, the staple cartridge 100 of the stapling head assembly 60 has a hollow cylindrical housing 240 which is tapered at its distal end. Preferably, the staple cartridge housing 240 is a one-piece molded plastic member. A hollow, generally cylindrical cartridge retainer 242 is inserted into the open proximal end of the staple cartridge housing 240. The cartridge retainer 242 has a pair of spring-like latch arms 244 located at diametrically opposed positions at the front of the retainer 242. The latch arms 244 are snap-fitted into a pair of diametrically opposed openings 245 adjacent to the proximal end of the cartridge housing 240 to hold the cartridge housing 240 and the retainer 242 together. The retainer 242 includes an annular flange 246 which is received in the annular grooves 228 of the clamshell members 221 and 222 to allow the staple cartridge 100 to rotate about its longitudinal axis relative to the support tube 70 and to the pivot connection 200. A set of twelve uniformly spaced circumferential teeth 248 is formed at the proximal end of the retainer 242. The teeth 248 are engaged by the detent arms 230 on the clamshell members 221 and 222. The detent arms 230 and teeth 248 provide a ratchet mechanism which allows the rotational orientation of the staple cartridge 100 to be adjusted in increments of 30 degrees.

Inside the staple cartridge 100 is mounted a staple forming mechanism comprising an anvil 250, a staple holder 252 and a staple former 254 which are preferably made of stainless steel. The staple former 254 is channel-shaped in configuration for slidably receiving the staple holder 252 therein. The staple former 254 has an elongated central slot 256 with a depending prong 258 at the proximal end of the slot 256. The staple holder 252 includes a depending prong 260 which is slidably received in the slot 256 and is biased away from the prong 258 by a compression coil spring 262. A feeder shoe 264 is slidably mounted within the staple cartridge 100 for urging a series of staples 65 toward the distal end of the cartridge 100. The feeder shoe 264 is biased in the distal direction by a compression coil spring 266 which is mounted on a distally projecting prong 268 on the cartridge retainer 242.

The staple driver 76 is connected to the staple former 254 by a plunger 270 which is slidably mounted between the clamshell members 221 and 222. The plunger 270 is a generally flat metal plate, e.g. aluminum, and includes a longitudinally extending side flange 272 slidably received in a longitudinal groove 274 formed in the clamshell member 222. The plunger 270 has a pivot hole 276 adjacent to its proximal end. A pivot link 278 includes a pair of laterally projecting pivot pins 280 and 282 which are pivotally received in the pivot holes 111 and 276, respectively, to attach the staple driver 76 to the plunger 270. The pivot link 278 transfers the longitudinal movement of the staple driver 76 into longitudinal movement of the plunger 270. Also, the pivot link 278 permits the plunger 270 to pivot relative to the staple driver 76. At the distal end of the plunger 270, a smaller diameter front disk 284 is spaced from a larger diameter rear disk 286. The front disk 284 is inserted between a pair of inwardly projecting fingers 288 at the proximal end of the staple former 254 to transfer the longitudinal movement of the plunger 270 into longitudinal movement of the staple former 254. The front disk 284 and the inwardly projecting fingers 288 permit the staple former 254 to rotate relative to the plunger 270.

Referring to FIG. 9, the staple cartridge housing 240 has an elongated hollow cylindrical wall 290 which preferably consists of transparent plastic material. Extending longitudinally inside the staple cartridge housing 240 is a first pair of elongated upstanding flanges 292 which are spaced apart and extend parallel to the longitudinal axis of the cylindrical wall 290. The elongated flanges 292 provide a set of guide rails for slidably supporting the staples 65 for longitudinal movement relative to the staple cartridge housing 240. Each flange or guide rail 292 has a ledge 293 (FIG. 10) which is inclined at an angle to the axis of the cartridge housing 240 and terminates in an extension 294 of the guide rail 292 at the open distal end of the cartridge housing 240. Each of the flanges 292 is spaced inwardly from the cylindrical wall 290 to provide a pair of elongated side channels 295 (FIG. 12) for receiving the depending legs 68 of the staples 65. The cartridge housing 240 includes a second pair of depending upper flanges 296 which are spaced apart and extend parallel to the longitudinal axis of the outer cylindrical wall 290. The upper flanges 296 terminate above the lower flanges 292 to provide a sufficient clearance therebetween to receive the crowns 66 of the staples 65. On the inside of each lower flange 292 is an elongated ledge 298 (FIG. 12) which slidably supports the staple former 254.

The staple cartridge housing 240 has a tapered nose 300 at its distal end including an internal horizontal ledge 302 provided with a longitudinal channel 304 for receiving the anvil 250 of the stapling head assembly 100. The ledge 302 has a rearwardly projecting post 306 to which the anvil 250 is secured. The tapered nose 300 has a central depending tab 308 located above the ledge 302 and provided with a downwardly sloped rear edge 309 which serves as a guide for the dimpled portion 67 of the staple 65 advanced by the staple forming mechanism. Also, the tapered nose 300 includes a pair of sloped ramps 310 (FIG. 11) on opposite sides of the central tab 308 for engaging the crown 66 of the staple 65 which is advanced by the staple forming mechanism to pivot the staple 65 into an orientation parallel to the longitudinal axis of the cartridge housing 240. Each of the ramps 310 terminates at a ledge 312 located adjacent to one of the extensions 294 of the guide rails 292. A window 314 is formed on each side of the cartridge housing 240 adjacent to one of the ramps 310 as a result of the molding process used to form the cartridge housing 240.

As shown in FIG. 9, the staple former 254 is an elongated, channel-shaped member provided with upstanding side flanges 320 extending along its opposite sides. The staple holder 252 is an elongated plate-like member which is slidably supported on the staple former 254 and located between the side flanges 320. The compression coil spring 262 normally biases the staple holder 252 distally relative to the staple former 254 with the depending prong 260 biased against the distal end of the elongated central slot 256. The staple holder 252 and the staple former 254 are inserted into the staple cartridge 240 between the lower upstanding flanges 292. The staple former 254 is slidably supported on the ledges 298 formed on the inside of the flanges 292. An ejector arm 322 extending from the distal end of the staple holder 252 has a notch 324 for receiving the dimpled portion 67 of the staple 65. A pusher finger 326 projects forwardly into the notch 324 at the distal end of the staple holder 252 for engaging the dimpled portion 67 of the staple 65 as the staple holder 252 is advanced to move the staple 65 into engagement with the anvil 250. The distal end of the ejector arm 322 is slanted away from and above the level of the pusher finger 326 and serves to disengage the staple 65 from the anvil 250 as the staple holder 252 is retracted after the staple 65 is formed. A pair of fingers 328 at the tip of the ejector arm 322 are spaced apart to receive the depending tab 308 of the cartridge housing 240 therebetween.

The anvil 250 includes a pair of laterally spaced prongs 330 (FIG. 9) at its distal end which allow the ejector arm 322 to pass therebetween when the staple holder 252 is advanced. Each prong 330 includes an inclined ramp 332 (FIG. 1a) for guiding the crown 66 of the staple 65 into engagement with the proximal side of the prong 330.

The staple follower 264 is channel-shaped and includes a generally flat top portion 340 which is slidably received between the lower flanges 292 and the upper flanges 296. The staple follower 264 also has a pair of depending side flanges 342 on its opposite sides which are received in the channels 295 adjacent to the lower flanges 292. The staple follower 264 includes a rearwardly projecting post 344 which is inserted into the distal end of the compression coil spring 266.

Referring to FIGS. 9 and 19, a stack of staples 65 is mounted in the staple cartridge housing 240 with the staple crowns 66 resting on and slidably supported by the elongated flanges or guide rails 292. The dimpled portions 67 of the staples 65 rest on top of the staple holder 252. The row of staples 65 is urged forwardly toward the distal end of the cartridge 240 by the staple follower 264 and the compression coil spring 266. The staple former 254 is biased rearwardly by the return spring 174 (FIG. 2) in the actuator handle assembly 80 to urge the depending prong 258, 295 against the front of the retainer 242. The staple holder 252 is biased forwardly by the compression coil spring 262 which urges the depending prong 260 against the front edge of the slot 256 in the staple former 254. The ejector arm 322 at the distal end of the staple holder 252 is located adjacent to the guide tab 308 at the front of the tapered nose 300 of the staple cartridge 240.

As shown in FIG. 19, the offset or dimpled portion 67 of the forwardmost staple 65 is located at a level different from the remaining staples 65 in the stack. The dimpled portion 67 of the forwardmost staple 65 is received in the notch 324 in front of the pusher finger 326. When the staple holder 252 is advanced, the dimpled portion 67 of the forwardmost staple 65 is advanced along the sloped surface 309 and adjacent to the guide tab 308 by the pusher finger 326. The top portion or crown 66 of the forwardmost staple 65 is advanced along a path between the inclined ramps 310 (FIG. 14) and the inclined ledges 293 of the guide rails 292 to rotate the staple 65 by 90 degrees about its dimpled portion 67.

Figure 20:
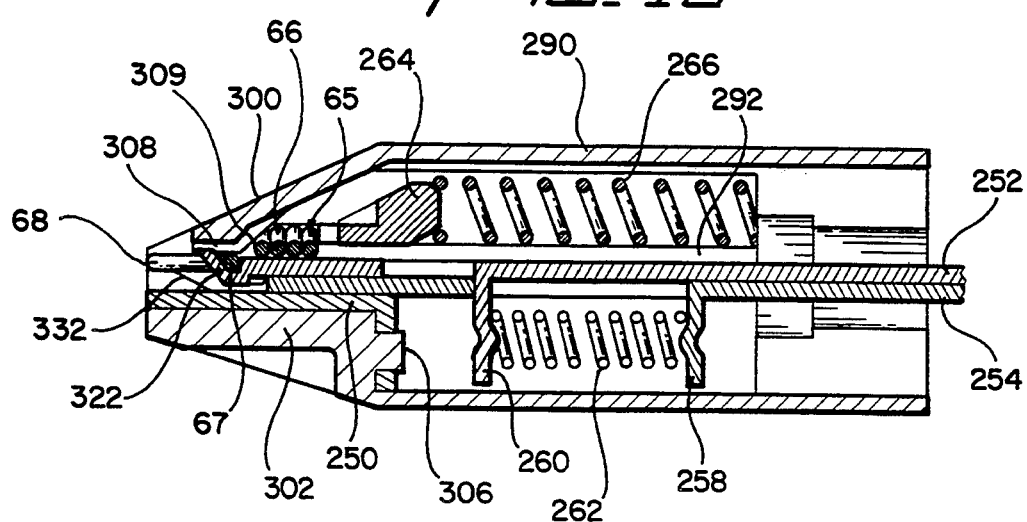
FIG. 20 is an enlarged longitudinal section of the staple cartridge of FIG. 9 showing the staple forming mechanism advanced to rotate a staple into a longitudinal orientation.
Figure 21:
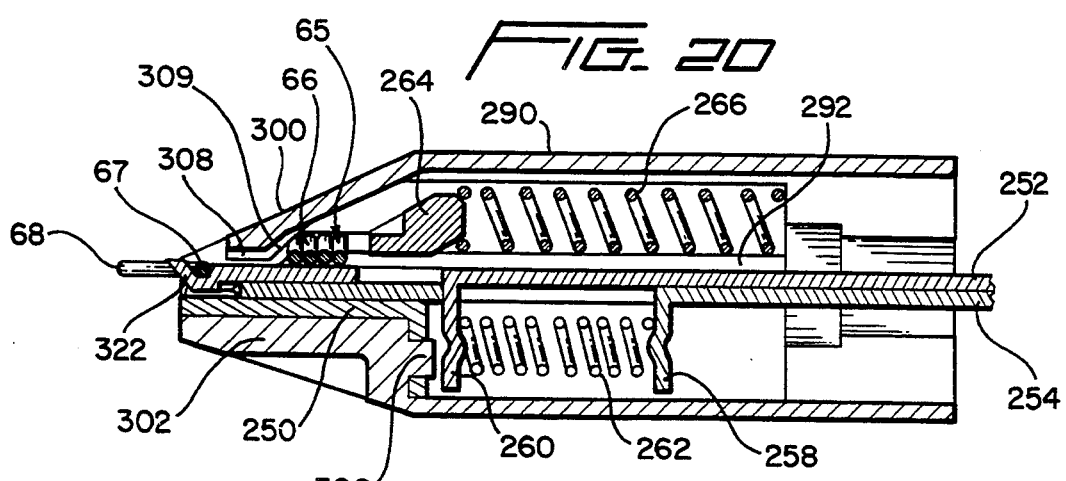
FIG. 21 is an enlarged longitudinal section of the staple cartridge of FIG. 9 showing the staple forming mechanism advanced to clamp the staple against an anvil of the staple cartridge.

As shown in FIG. 20, with the staple holder partially advanced, the forwardmost staple 65 is rotated into a longitudinal orientation with its staple legs 68 parallel to the longitudinal axis of the staple cartridge housing 240. Thereafter, as shown in FIG. 21, when the staple holder 252 is fully advanced, the forwardmost staple 65 travels along the extensions 294 of the guide rails 292 and is clamped against the anvil prongs 330 with the staple legs 68 projecting distally from the front of the staple cartridge housing 240. The remaining staples 65 in the stack are restrained by the top of the staple holder 252 which engages the dimpled portions 67 of the staples 65.

The staple forming mechanism of the staple cartridge 100 is actuated by squeezing the staple actuating lever 88 toward the handle grip 86. As a result, the staple actuating lever 88 is pivoted about the pivot pin 96 and the upright fingers 170 advance the slide member 154 in the distal direction. The slide member 154 advances the staple driver 76 in the distal direction which, in turn, advances the plunger 270 to actuate the staple holder 252 and the staple former 254. After the staple holder 252 and the staple former 254 are fully advanced to form one of the staples 65, the staple actuating lever 88 is released and returned to its original position by the return coil spring 174, which retracts the slide block 154 and the staple driver 76.

Figure 22:
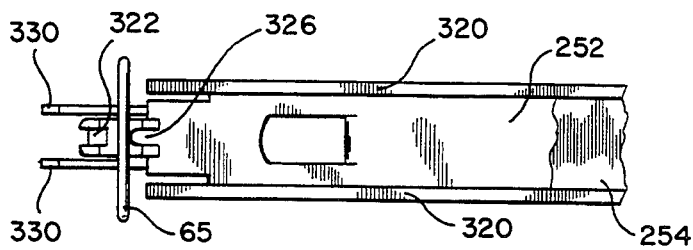
FIGS. 22-26 illustrate the operation of the staple forming mechanism in advancing and forming a staple.

The operation of the staple forming mechanism is illustrated in FIGS. 22–26 which, for clarity, show only one staple 65. FIG. 22 shows the staple 65 positioned in the notch 324 in front of the pusher finger 326 at the start of the staple forming cycle which corresponds to the position of the staple holder 252 and staple former 254 shown in FIG. 19. Initially, when the staple actuating lever 88 is actuated, the staple holder 252 and the staple former 254 are advanced simultaneously to advance the staple 65 toward the prongs 330 of the anvil 250. As the staple 65 is advanced toward the anvil prongs 330, the staple 65 is rotated by 90 degrees into a longitudinal orientation (FIG. 20) with the staple legs 68 pointing distally.

Figure 23:
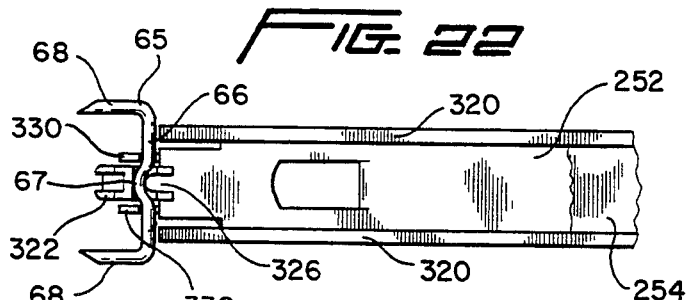

FIG. 23 shows the staple holder 252 and the staple former 254 advanced to a staple clamping position corresponding to FIG. 21 in which the staple crown 66 is clamped between the pusher finger 326 and the prongs 330 of the anvil 250. Thereafter, as the staple actuating lever 88 is actuated, only the staple former 254 is advanced while the staple holder 252 remains stationary with the staple 65 clamped against the anvil prongs 330.

Figure 24:
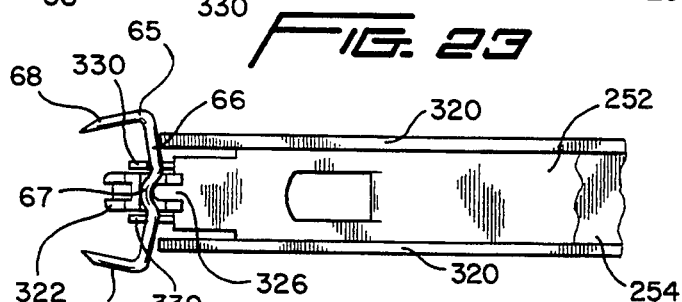

FIG. 24 shows the initial movement of the staple former 254 relative to the staple holder 252 to form the staple 65 about the anvil prongs 330. The initial contact of the former flanges 320 with the staple 65 results in a slight bending of the staple crown 66 with the staple legs 68 angled toward each other.

Figure 25:
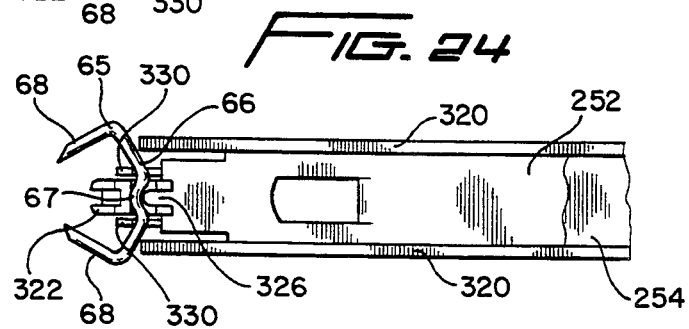
Figure 26:
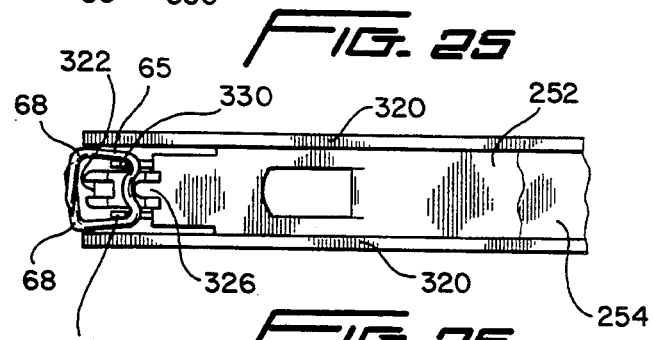

FIG. 25 shows an intermediate stage of the staple forming cycle in which the former flanges 320 are further advanced to bend the staple crown 66 around the anvil prongs 330 to bring the staple legs 68 closer together. FIG. 26 shows the final stage of the staple forming cycle in which the former flanges 320 are fully advanced to bend the staple legs 68 into an overlapping configuration to secure the staple 65 to the tissue.

After the staple 65 is completely formed, the staple actuating lever 88 is released and the staple former 254 is moved rearwardly relative to the staple holder 252 by the compression coil spring 262. When the depending lug 260 of the stapler holder 252 is engaged (as shown in FIG. 21) by the front edge of the slot 256 of the staple former 254 (FIG. 9), the staple holder 252 and the staple former 254 are retracted together by the return spring 174 in the actuator handle assembly 80. The ejector arm 322 lifts the formed staple 65 from the anvil prongs 330 as the staple holder 252 is retracted. The staple holder 252 and the staple former 254 are returned to the start position shown in FIG. 19 where the next staple 65 is received in the notch 324 in front of the pusher finger 326. Then, the staple forming cycle is repeated to form the next staple 65.

The actuator handle assembly 80 includes a precock ratchet mechanism comprising the ratchet spring 178 (FIGS. 5 and 27-31) and the ratchets 182 which prevents the retraction of the staple forming mechanism until the staple 65 is completely formed. The operation of the ratchet mechanism is illustrated in FIGS. 27-31 which show the various ratchet positions corresponding to the stages of the staple forming cycle shown in FIGS. 22-26, respectively.

Figure 27:
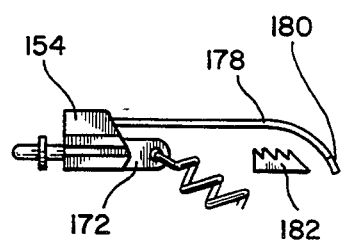
FIGS. 27–31 are fragmentary views showing the operation of a precock ratchet mechanism in the actuator handle assembly.
Figure 28:
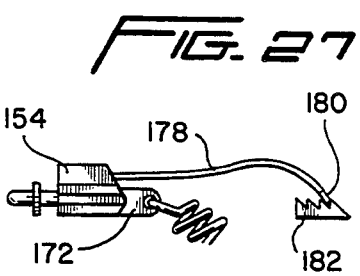

As shown in FIG. 27, each spring arm 180 of the ratchet spring 178 is initially disengaged from each ratchet 182 with the staple holder 252 and the staple former 254 located in the retracted position (FIG. 22). As shown in FIG. 28, each spring arm 180 of the ratchet spring 178 is engaged in the first notch of each ratchet 182 with the staple holder 252 and the staple former 254 in the advanced position (FIG. 23) in which the staple 65 is clamped against the anvil prongs 330. Thereafter, the engagement of the ratchet spring arms 180 with the ratchets 182 prevents the staple holder 252 and the staple former 254 from being retracted until the staple forming cycle is completed.

Figure 29:
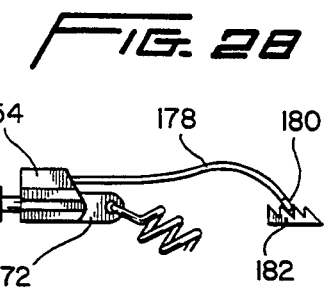
Figure 30:
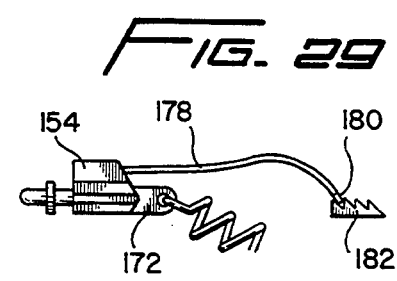

As shown in FIG. 29, each spring arm 180 of the ratchet spring 178 is engaged in the second notch of each ratchet 182 with the flanges 320 of the staple former 254 initially engaged with the staple crown 66 to begin the forming of the staple 65 (FIG. 24). As shown in FIG. 30, each spring arm 180 of the ratchet spring 178 is engaged in the third notch of each ratchet 182 with the former flanges 320 advanced to the intermediate stage of the staple forming cycle (FIG. 25) in which the staple legs 68 are partially closed.

Figure 31:
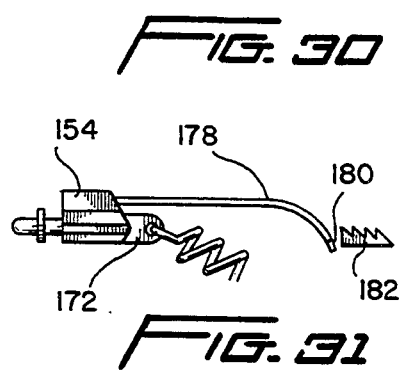
Figure 37:
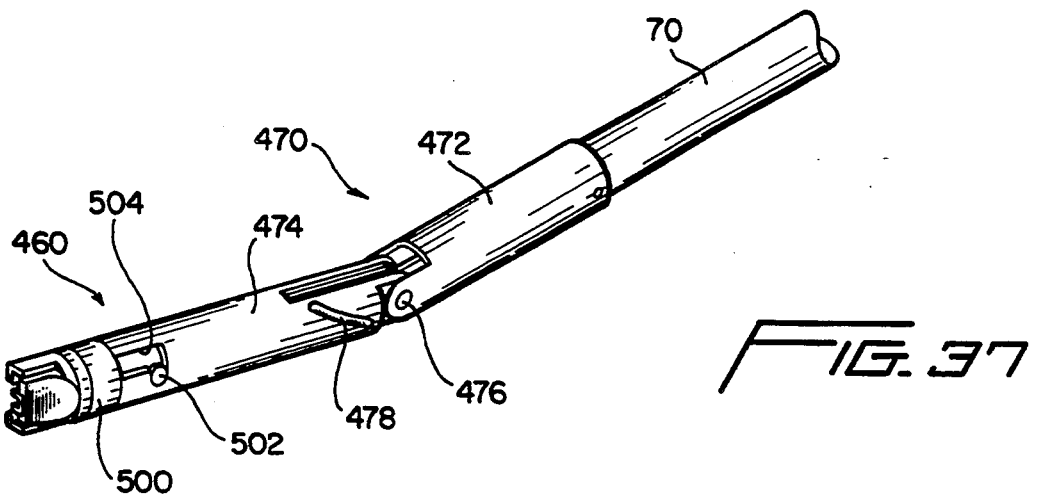
FIG. 37 is a perspective view of another embodiment of a stapling head assembly for use with the surgical stapling instrument of this invention.
Figure 38:
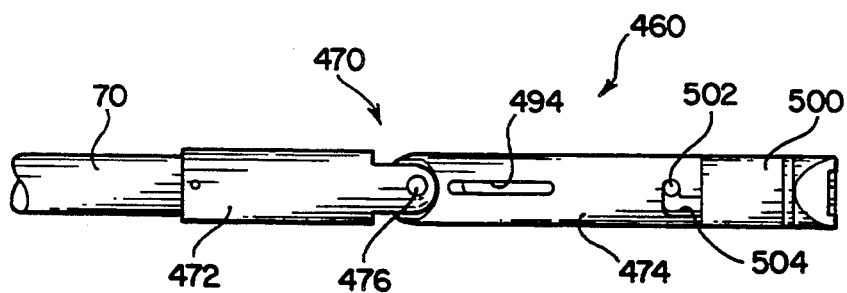
FIG. 38 is a side view of the stapling head assembly from the opposite side of FIG. 37.

As shown in FIG. 31, each spring arm 180 of the ratchet spring 178 is disengaged from each ratchet 182 with the former flanges 320 fully advanced (FIG. 26) to bend the staple legs 68 into an overlapping relationship. Each spring arm 180 travels rearwardly adjacent to the unnotched side of the corresponding ratchet 182 to allow the ratchet spring 178 to return to its retracted position (FIG. 27) when the staple actuating lever 88 is released.

In performing a hernia repair procedure, the endoscopic surgical stapling instrument 50 is inserted into a body cavity through a trocar tube or cannula installed in a body wall. Initially, the surgical stapling instrument 50 is introduced into the body cavity in its non-articulated mode, i.e., with the staple cartridge 100 aligned with the longitudinal axis of the support tube 70. An endoscope may be inserted into the body cavity through a separate trocar tube or cannula for observation of the surgical site. The stapling cartridge 100 is positioned in the desired orientation over the surgical site by operating the rotatable adjusting knob 82 and the saddle-shaped actuator 84 to adjust the rotational orientation of the support tube 70 and the angular orientation of the staple cartridge 100. The staple cartridge 100 can be articulated to angles of 15, 30, 45 and 60 degrees relative to the support tube 70 by retracting the saddle-shaped actuator 84.

If it is desired to change the rotational orientation of the staple cartridge 100 on its axis, the staple cartridge 100 is returned to the non-articulated mode by sliding the saddle-shaped actuator 84 forwardly. The surgical stapling instrument 50 is withdrawn from the trocar tube or cannula and the staple cartridge 100 is rotated manually relative to the support tube 70. Then, the surgical stapling instrument 50 is reintroduced into the body cavity in its non-articulated mode and the orientation of the staple cartridge 100 is adjusted by operating the rotatable adjusting knob 82 and the saddle-shaped actuator 84.

With the staple cartridge 100 adjusted to the desired orientation, the staple actuator lever 88 is squeezed to actuate the staple forming mechanism in the staple cartridge 100 to fasten one of the staples 65 to the tissue at the surgical site. Thereafter, the staple cartridge 100 is shifted to another location and the operation is repeated to fasten another staple 65 to the tissue. When the staple actuator lever 88 is released, the formed staple 65 is disengaged from the anvil 250 of the staple cartridge 100.

Referring to FIG. 18, the surgical stapling instrument 50 can be used to secure a hernia patch 62 at a desired surgical site. The hernia patch 62 is attached to internal body tissue 64 by applying a series of staples 65 to the edges of the hernia patch 62. The staple cartridge 100 is readily adjustable into the different orientations to apply the staples 65 at various locations along the edges of the hernia patch 62.

FIGS. 32 and 33 illustrate an alternative embodiment of the surgical stapling instrument, generally 350, including a distal stapling head assembly 360 which is pivotally connected to an elongated support tube 370 rotatably mounted on a proximal actuator handle assembly 380. A rotatable adjusting knob 382 is mounted at the distal end of the actuator handle assembly 380 for rotating the support tube 370 about its longitudinal axis. A saddle-shaped actuator 384 is slidably mounted on the actuator handle assembly 380 for controlling the pivotal movement of the stapling head assembly 360 relative to the support tube 370. The actuator handle assembly 380 has a depending handle grip 386 and a pivotally mounted staple actuating lever 388 for actuating the stapling head assembly 360. The internal components of the stapling head assembly 360, the support shaft 370 and the actuator handle assembly 380 are substantially identical to the corresponding components of the surgical stapling instrument 50 described above. Accordingly, no detailed description of the internal components of the surgical stapling instrument 350 is necessary, and it will be understood by persons skilled in the art that the previous description of the internal components of the surgical stapling instrument 50 is applicable to the internal components of the surgical stapling instrument 350, unless otherwise described.

The stapling head assembly 360 includes a rotatably mounted staple cartridge 400 which is substantially identical in construction to the stapling cartridge 100 described above. The stapling head assembly 360 is pivotally mounted on the support tube 370 by a pivot connection 390 which is substantially identical to the pivot connection 200 described above.

As shown in FIG. 33, the handle assembly 380 includes a pair of hollow handle sections 392 which are adapted to snap fit together. Each of the handle sections 392 includes a distally extending elongated, semi-cylindrical neck portion 394 in which the proximal end of the support tube 370 is received and mounted for rotation about its longitudinal axis relative to the handle assembly 380. Each of the handle sections 392 includes an internal annular flange 395 (one shown) for engaging a radially projecting flange 372 at the proximal end of the support tube 370 to retain the support tube 370 within the handle assembly 380. The staple actuating lever 388 is pivotally mounted on the actuator handle assembly 380 by a pivot pin 396.

As shown in FIGS. 32 and 33, the adjusting knob 382 comprises a pair of elongated, hollow tapered sleeve-like sections 402 which fit together over the neck portions 394 of the handle sections 392. Each of the sleeve-like knob sections 402 has an inwardly projecting prong 403 adjacent to its distal end. The prongs 403 are received in a pair of holes formed on opposite sides of the support tube 370 to secure the knob sections 402 to the support tube 370. The actuator handle assembly 380 and the adjusting knob 382 include the same ratchet mechanism, described above in connection with the stapling instrument 50, which allows the adjusting knob 382 to rotate the support shaft 370 about its longitudinal axis in sixteen equal intervals of 22½ degrees. Each of the knob sections 402 has an enlarged rear section 407 provided with alternating longitudinal ridges 408 and finger receiving grooves 409 which facilitate the rotation of the adjusting knob 382 and the support tube 370 by the surgeon.

The actuator handle assembly 380 includes a rotatable control knob 410 for controlling the rotation of the staple cartridge 400 about its longitudinal axis relative to the support shaft 370. The control knob 410 includes an elongated hollow, conically tapered portion 412 which is rotatably received between the sleeve-like sections 402 of the adjusting knob 382 and the cylindrical neck portions 394 of the handle sections 392. A hollow cylindrical, internally toothed geneva gear wheel 414 is secured within the distal end of the conically tapered body 412 for rotation with the control knob 410. A first pinion gear 416 which is rotatably mounted on the inside of the support tube 370 extends through a window 372 (FIG. 35) formed in the side of the support tube 370 and engages the internal teeth on the geneva gear wheel 414. The pinion gear 416 is attached to a flexible cable 418 which extends longitudinally through the support shaft 370 and the pivot connection 390. The distal end of the flexible cable 418 is connected to a second pinion gear 420 rotatably supported in a bushing 422 (FIG. 34) mounted on the inside of one of the clamshell members 424 forming part of the pivot connection 390. The flexible cable 418 is formed of conventional materials such as steel alloys. The staple cartridge 400 is mounted on a cylindrical retainer 426 which is rotatably supported by the clamshell members 424 of the pivot connection 390. The cartridge retainer 422 has an internally toothed geneva gear wheel 428 (FIG. 36) at its proximal end which engages the pinion gear 420.

In the operation of the surgical stapling instrument 350, the control knob 410 is used to control the rotational orientation of the staple cartridge 400 relative to the support shaft 370 and the pivot connection 390. The rotation of the control knob 410 is transmitted via the flexible cable 418 to the cartridge retainer 422 which rotates the staple cartridge 400 about its axis. As a result, the rotational orientation of the staple cartridge 400 relative to the support shaft 370 is adjustable by the rotation of the control knob 410.

Except for the control knob 410 which rotates the staple cartridge 400, the surgical stapling instrument 350 operates in substantially the same manner as the stapling instrument 50 described above. The rotatable adjusting knob 382 is used to rotate the support shaft 370 relative to the actuator handle assembly 380. The saddle-shaped actuator 384 is slidable longitudinally along the actuator handle assembly 380 to pivot the stapling head assembly 360 about an axis transverse to the longitudinal axis of the support shaft 370. The staple actuating lever 388 is pivoted to actuate the staple forming mechanism of the staple cartridge 400 in substantially the same manner as described above.

FIGS. 37–40 show an alternative embodiment of a stapling head assembly, generally 460, which can be used with the surgical stapling instrument 50 described above. The stapling head assembly 460 is pivotally mounted at the distal end of the support tube 70 by a pivot connection 470 including a tubular pivot housing 472 secured to the support tube 70 and a tubular cartridge support member 474 pivotally connected to the pivot housing 472 by a pair of pivot pins 476 extending laterally from opposite sides of the cartridge support member 474. An inclined slot 478 is formed on one side of the cartridge support member 474.

A staple cartridge 500 is mounted at the distal end of the cartridge support member 474. The staple cartridge 500 is generally cylindrical in shape and is adapted to be received in the open distal end of the cartridge support member 474. The staple cartridge 500 has a pair of latch pins 502 projecting radially outward its opposite sides. The latch pins 502 are received and latched in a pair of slots 504 extending longitudinally from the distal end of the cartridge support member 474. The latch pins 502 and slots 504 allow the staple cartridge 500 to be disengaged from the cartridge support member 474 when it is desired to replace the staple cartridge 500.

Figure 40:
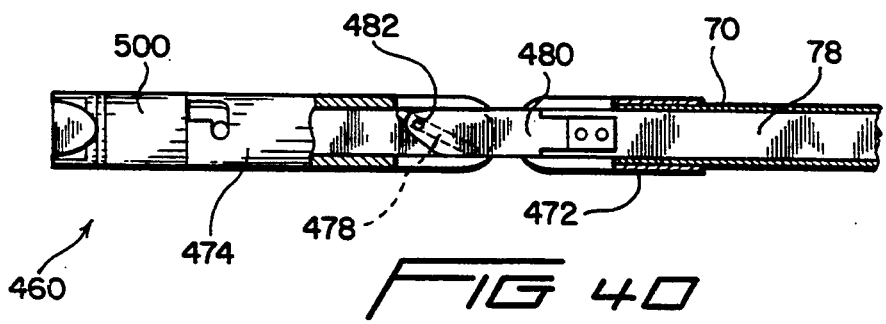
FIG. 40 is a partially cutaway side view of the stapling head assembly from the opposite side of FIG. 39.

As shown FIG. 40, an articulation control member 480 is slidably mounted in the pivot housing 472 and is connected to the articulation driver 78. A laterally projecting guide pin 482 is located adjacent to the distal end of the articulation control member 480 and is slidably received in the inclined slot 478 of the cartridge support member 474. The inclined slot 478 and the guide pin 482 convert longitudinal movement of the articulation driver 78 into pivotal movement of the stapling head assembly 460 about the pivot pins 476.

Figure 39:
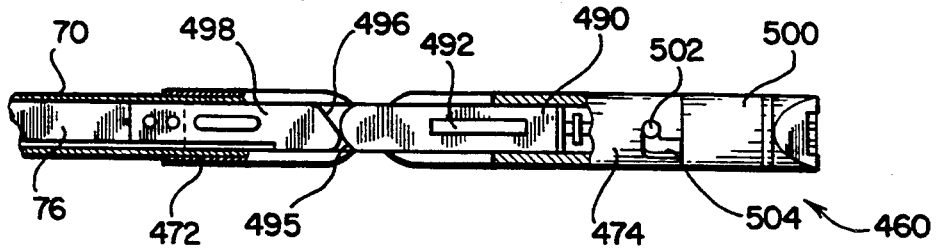
FIG. 39 is a partially cutaway side view of the stapling head assembly of FIG. 38.

As shown in FIG. 39, a plunger 490 is slidably mounted for longitudinal movement in the cartridge support member 474. The plunger 490 includes an elongated laterally projecting side flange 492 which is slidably received in a longitudinal slot 494 (FIG. 38) formed on the side of the cartridge support member 474. The plunger 490 has a semi-circular rear edge 495 which is engaged by an inclined cam surface 496 on a drive member 498 mounted at the distal end of the staple driver 76. The front end of the plunger 490 is engaged with the staple forming mechanism inside the staple cartridge 500.

When the staple driver 76 is advanced in the distal direction, the plunger 490 is advanced to actuate the staple forming mechanism of the staple cartridge 500 which operates in substantially the same manner as described above. The semi-circular rear edge 496 of the plunger 90 and the inclined cam surface 498 at the distal end of the staple driver 76 allow the staple forming mechanism to be actuated in any angular orientation of the staple cartridge 500.

The invention in its broader aspects is not limited to the specific details of the preferred embodiments shown and described, and those skilled in the art will recognize that the invention can be practiced with modification within the spirit and scope of the appended claims.

We claim:

1. A surgical stapling instrument for applying one or more surgical staples to tissue, said instrument comprising:

a handle including a staple actuator mechanism;

an elongated tubular support shaft having a longitudinal axis and extending from said handle, said support shaft being mounted to said handle and having a rotating mechanism controlling rotation about said longitudinal axis relative to said handle;

a staple cartridge mounted at the distal end of said support shaft for holding a plurality of staples and including a staple forming mechanism connected to said staple actuator mechanism for applying the staples to the tissue;

pivot means at the distal end of said support shaft for mounting said staple cartridge for pivotal movement about an axis transverse to said longitudinal axis of said support shaft and which includes actuator means on said handle for pivoting said staple cartridge about said transverse axis to adjust the angular position of said staple cartridge relative to said support shaft; and an articulation driver slidably mounted for longitudinal movement in said support shaft for connecting said actuator means to said pivot means to pivot said staple cartridge relative to said support shaft, said articulation driver including a guide pin at its distal end received in an arcuate groove in said pivot means for converting the longitudinal movement of said articulation driver into pivotal movement of said staple cartridge relative to said support shaft.

2. An endoscopic surgical stapling instrument for applying one or more surgical staples to internal body tissue comprising:

an actuator handle assembly including a staple actuator mechanism;

an elongated tubular support shaft having a longitudinal axis and extending from said actuator handle assembly, said support shaft being mounted to said actuator handle assembly and including a shaft rotation mechanism controlling rotation of said shaft about its longitudinal axis relative to said actuator handle assembly;

a staple cartridge mounted at the distal end of said support shaft for holding a plurality of staples and including a staple forming mechanism connected to said staple actuator mechanism for applying the staples to the tissue, said staple cartridge having a circumferential cross-section no greater than said shaft cross-section;

pivot means at the distal end of said support shaft for mounting said staple cartridge for pivotal movement relative to said support shaft about an axis transverse to said longitudinal axis of said support shaft;

cartridge rotating means for rotating said staple cartridge relative to said support shaft about a cartridge axis defined along the length of said cartridge;

staple driver means drivingly engaged with said staple actuator mechanism for being operated by said staple actuator mechanism when said staple cartridge is at any angular position relative to said shaft, said staple driver means comprising:

a staple driver suitably mounted for longitudinal movement in said support shaft and coupled to said staple actuator mechanism; and a plunger slidably mounted on said pivot means and actuated by the longitudinal movement of said staple driver for actuating the staple forming mechanism when said staple actuator mechanism is operated.

3. The stapling instrument of claim 2, which includes:

a pivot link for connecting said plunger to said staple driver to permit said staple forming mechanism to pivot relative to said staple driver.

4. The stapling instrument of claim 2, wherein:

said plunger is coupled to said staple forming mechanism for longitudinal movement therewith and is adapted to permit said staple forming mechanism to rotate about the longitudinal axis of said staple cartridge relative to said plunger.

5. An endoscopic surgical stapling instrument for applying one or more surgical staples to internal body tissue comprising:

an actuator handle assembly including a staple actuator mechanism;

an elongated tubular support shaft having a longitudinal axis and extending from said actuator handle assembly, said support shaft being mounted to said actuator handle assembly and including a shaft rotation mechanism controlling rotation of said shaft about its longitudinal axis relative to said actuator handle assembly;

a staple cartridge mounted at the distal end of said support shaft for holding a plurality of staples and including a staple forming mechanism connected to said staple actuator mechanism for applying the staples to the tissue, said staple cartridge having a circumferential cross-section no greater than said shaft cross-section;

pivot means at the distal end of said support shaft for mounting said staple cartridge for pivotal movement relative to said support shaft about an axis transverse to said longitudinal axis of said support shaft;

cartridge rotating means for rotating said staple cartridge relative to said support shaft about a cartridge axis defined along the length of said cartridge;

actuator means on said handle assembly for pivoting said staple cartridge relative to said support shaft about said transverse axis; and an articulation driver slidably mounted for longitudinal movement in said support shaft for connecting said actuator means to said pivot means to pivot said staple cartridge relative to said support shaft, said articulation driver including a guide pin at its distal end received in an arcuate groove in said pivot means for converting the longitudinal movement of said articulation driver into pivotal movement of said staple cartridge relative to said support shaft.

6. An endoscopic surgical stapling instrument for applying one or more surgical staples to internal body tissue comprising:

an actuator handle assembly including a staple actuator mechanism;

an elongated tubular support shaft having a longitudinal axis and extending from said actuator handle assembly, said support shaft being mounted to said actuator handle assembly and including a shaft rotation mechanism controlling rotation of said shaft about its longitudinal axis relative to said actuator handle assembly;

a staple cartridge mounted at the distal end of said support shaft for holding a plurality of staples and including a staple forming mechanism connected to said staple actuator mechanism for applying the staples to the tissue, said staple cartridge having a circumferential cross-section no greater than said shaft cross-section;

pivot means at the distal end of said support shaft for mounting said staple cartridge for pivotal movement relative to said support shaft about an axis transverse to said longitudinal axis of said support shaft;

cartridge rotating means for rotating said staple cartridge relative to said support shaft about a cartridge axis defined along the length of said cartridge;

actuator means on said handle assembly for pivoting said staple cartridge relative to said support shaft about said transverse axis;

an articulation driver slidably mounted for longitudinal movement in said support shaft for connecting said actuator means to said pivot means to pivot said staple cartridge relative to said support shaft; said actuator means comprising:

a slide member mounted for longitudinal movement on said actuator handle assembly; and a coupling member for connecting said slide member to said articulation driver for transmitting the longitudinal movement of said slide member to said articulation driver to pivot said staple cartridge.

7. The stapling instrument of claim 6, wherein:
said articulation driver is free to rotate relative to said slide member.

8. A surgical stapling instrument for applying one or more surgical staples to tissue, said instrument comprising:

a handle including a staple actuator mechanism;

a tubular support shaft having a longitudinal axis and a circumferential cross-section and extending from said handle;

a staple cartridge carried on said support shaft and connected to said staple actuator mechanism for applying one or more staples seriatim to the tissue, said staple cartridge when mounted on said shaft having a circumferential cross-section no greater than said shaft cross-section;

a pivot connection structure connecting said said staple cartridge to said support shaft for accommodating pivotal movement of said cartridge about an axis transverse to said longitudinal axis of said support shaft;

a pivot actuator located on said handle and operative to effect the pivoting of said staple cartridge; and cartridge rotating means on said shaft for rotating said staple cartridge relative to said support shaft about a cartridge axis defined along the length of said cartridge;

said pivot connection structure including a pivotable housing that is pivotable relative to said support shaft;

said staple cartridge being mounted to said pivotable housing for rotation about said cartridge axis, said staple cartridge including a hollow cartridge housing containing a staple advancing and forming mechanism operatively connected to said staple actuator mechanism, said staple advancing and forming mechanism including a former that is longitudinally reciprocatable within said hollow cartridge housing; and said former having a proximal end for rotatably engaging said staple actuator mechanism to accommodate rotation of said former about the cartridge axis relative to said support shaft and said staple actuator mechanism.

9. A surgical stapling instrument for applying one or more surgical staples to tissue, said instrument comprising:

a handle including a staple actuator mechanism;

a tubular support shaft having a longitudinal axis and a circumferential cross-section and extending from said handle;

a staple cartridge carried on said support shaft and connected to said staple actuator mechanism for applying one or more staples seriatim to the tissue, said staple cartridge when mounted on said shaft having a circumferential cross-section no greater than said shaft cross-section;

a pivot connection structure connecting said staple cartridge to said support shaft for accommodating pivotal movement of said cartridge about an axis transverse to said longitudinal axis of said support shaft;

a pivot actuator located on said handle and operative to effect the pivoting of said staple cartridge; and cartridge rotating means on said shaft for rotating said staple cartridge relative to said support shaft about a cartridge axis defined along the length of said cartridge;

said pivot connection structure including a pivotable housing that is pivotable relative to said support shaft;

said staple cartridge being mounted to said pivotable housing for rotation about said cartridge axis, said staple cartridge including a hollow cartridge housing containing a staple advancing and forming mechanism operatively connected to said staple actuator mechanism, said staple advancing and forming mechanism including a former that is longitudinally reciprocatable within said hollow cartridge housing; and said instrument further including a retainer having
(A) a proximal end received in said pivotable housing to accommodate rotation of said retainer relative to said pivotable housing; and
(B) a distal end received in said hollow cartridge housing with a latch to prevent relative rotation between said retainer and said hollow cartridge housing.

10. A surgical stapling instrument for applying one or more surgical staples to tissue, said instrument comprising:

a handle including a staple actuator mechanism;

a tubular support shaft having a longitudinal axis and a circumferential cross-section and extending from said handle;

a staple cartridge carried on said support shaft and connected to said staple actuator mechanism for applying one or more staples seriatim to the tissue, said staple cartridge when mounted on said shaft having a circumferential cross-section no greater than said shaft cross-section;

a pivot connection structure connecting said staple cartridge to said support shaft for accommodating pivotal movement of said cartridge about an axis transverse to said longitudinal axis of said support shaft;

a pivot actuator located on said handle and operative to effect the pivoting of said staple cartridge; and cartridge rotating means on said shaft for rotating said staple cartridge relative to said support shaft about a cartridge axis defined along the length of said cartridge;

said staple cartridge including a cartridge housing that contains a staple storage, advancing, and forming system and a plurality of staples each having
(A) a generally U-shaped body including a crown with a central offset portion between two non-offset portions;
(B) a pair of legs at opposite ends of said crown depending from said non-offset portions, said staples being arranged in a side-by-side stack oriented transversely to the cartridge axis with the staple legs oriented perpendicularly to the cartridge axis; and said staple storage, advancing, and forming system including a staple advancing and forming mechanism that is operatively engaged with said staple actuator mechanism and that is adapted for engaging the distalmost staple to advance the distalmost staple distally to effect engagement of part of said staple crown with a part of said cartridge housing whereby the staple rotates about ninety degrees to an orientation with the staple legs oriented parallel to the cartridge axis.

11. A surgical stapling instrument for applying one or more surgical staples to tissue, said instrument comprising:

a handle including a staple actuator mechanism;

a tubular support shaft having a longitudinal axis and a circumferential cross-section and extending from said handle;

a staple cartridge carried on said support shaft and connected to said staple actuator mechanism for applying one or more staples seriatim to the tissue, said staple cartridge when mounted on said shaft having a circumferential cross-section no greater than said shaft cross-section;

a pivot connection structure connecting said staple cartridge to said support shaft for accommodating pivotal movement of said cartridge about an axis transverse to said longitudinal axis of said support shaft;

a pivot actuator located on said handle and operative to effect the pivoting of said staple cartridge; and cartridge rotating means on said shaft for rotating said staple cartridge relative to said support shaft about a cartridge axis defined along the length of said cartridge;

said staple cartridge including a hollow cartridge housing containing a plurality of staples and a staple advancing and forming mechanism for moving one of said staples toward the distal end of said cartridge and forming the staple;

each said staple having a generally U-shaped body including a crown with a central offset portion between two non-offset portions and a pair of legs at opposite ends of said crown each depending from one of said non-offset portions; and said staple cartridge housing including:

a staple storage region defined by a guide surface for supporting and guiding said staple crowns and includes a cavity for receiving said staple legs, said staples being arranged in a side-by-side stack in said storage region with each staple oriented transversely to the cartridge axis with the staple legs oriented perpendicularly to the cartridge axis;

a staple feeder shoe in said storage region and a spring biasing said feeder shoe distally along the length of said cartridge to engage the most proximal staple in said stack and urge said stack distally;

an inclined surface and an inclined ramp spaced from said inclined surface for receiving therebetween the distalmost staple from the stack at the distal end of said guide surface, said inclined surface and ramp each being oriented at an oblique angle relative to said cartridge axis; and spaced-apart extension surfaces for receiving said staple crown as said staple advances distally from said inclined surface and inclined ramp whereby either said offset portion or said non-offset portions engage said ramp to rotate said staple about 90° into an orientation with the staple legs oriented parallel to said cartridge axis and pointing toward the distal end of said, cartridge.

12. An endoscopic surgical stapling instrument for applying one or more surgical staples to internal body tissue, said instrument comprising:

an actuator handle assembly including a staple actuator mechanism;

an elongated tubular support shaft having a longitudinal axis and extending from said actuator handle assembly, said support shaft being mounted to said actuator handle assembly and including a first rotation mechanism controlling rotation of said shaft about its longitudinal axis relative to said actuator handle assembly;

a staple cartridge mounted at the distal end of said support shaft for holding a plurality of staples and including a staple forming mechanism connected to said staple actuator mechanism for applying the staples to the tissue;

pivot means at the distal end of said support shaft for mounting said staple cartridge for pivotal movement relative to said support shaft about an axis transverse to said longitudinal axis of said support shaft;

a second rotation mechanism controlling rotation of said cartridge about its longitudinal axis relative to said pivot means and to said support shaft;

actuator means on said handle assembly for pivoting said staple cartridge relative to said support shaft about said transverse axis; and an articulation driver slidably mounted for longitudinal movement in said support shaft for connecting said actuator means to said pivot means to pivot said staple cartridge relative to said support shaft, said articulation driver including a guide pin at its distal end received in an arcuate groove in said pivot means for converting the longitudinal movement of said articulation driver into pivotal movement of said staple cartridge relative to said support shaft.

13. An endoscopic surgical stapling instrument for applying one or more surgical staples to internal body tissue, said instrument comprising:

an actuator handle assembly including a staple actuator mechanism;

an elongated tubular support shaft having a longitudinal axis and extending from said actuator handle assembly, said support shaft being mounted to said actuator handle assembly and including a first rotation mechanism controlling rotation of said shaft about its longitudinal axis relative to said actuator handle assembly;

a staple cartridge mounted at the distal end of said support shaft for holding a plurality of staples and including a staple forming mechanism connected to said staple actuator mechanism for applying the staples to the tissue;

pivot means at the distal end of said support shaft for mounting said staple cartridge for pivotal movement relative to said support shaft about an axis transverse to said longitudinal axis of said support shaft;

a second rotation mechanism controlling rotation of said cartridge about its longitudinal axis relative to said pivot means and to said support shaft;

actuator means on said handle assembly for pivoting said staple cartridge relative to said support shaft about said transverse axis; and an articulation driver slidably mounted for longitudinal movement in said support shaft for connecting said actuator means to said pivot means to pivot said staple cartridge relative to said support shaft, said articulation driver including at its distal end one of a guide pin and arcuate groove, said pivot means including the other of said guide pin and arcuate groove, said guide pin being received in said arcuate groove for converting the longitudinal movement of said articulation driver into pivotal movement of said staple cartridge relative to said support shaft.

* * * * *